United States Patent
Troy et al.

(10) Patent No.: US 9,234,904 B2
(45) Date of Patent: Jan. 12, 2016

(54) AUTONOMOUS NON-DESTRUCTIVE EVALUATION SYSTEM FOR AIRCRAFT STRUCTURES

(71) Applicant: The Boeing Company, Chicago, IL (US)

(72) Inventors: James J. Troy, Issaquah, WA (US); Gary Ernest Georgeson, Tacoma, WA (US); Karl Edward Nelson, Shoreline, WA (US); Scott Wesley Lea, Renton, WA (US)

(73) Assignee: THE BOEING COMPANY, Chicago, IL (US)

(*) Notice: Subject to any disclaimer, the term of this patent is extended or adjusted under 35 U.S.C. 154(b) by 180 days.

(21) Appl. No.: 14/149,887

(22) Filed: Jan. 8, 2014

(65) Prior Publication Data

US 2014/0200832 A1    Jul. 17, 2014

Related U.S. Application Data

(63) Continuation of application No. 13/160,238, filed on Jun. 14, 2011, now Pat. No. 8,713,998.

(51) Int. Cl.
*G01N 21/00* (2006.01)
*G01N 35/00* (2006.01)
(Continued)

(52) U.S. Cl.
CPC ........ G01N 35/00584 (2013.01); B64F 5/0045 (2013.01); G01N 21/00 (2013.01);
(Continued)

(58) Field of Classification Search
CPC .............. G01N 27/90; G01N 21/9515; G01N 2021/9518; G01N 21/00; G01N 27/00; B64F 5/0045

USPC .......................... 73/104, 105, 112.01, 118.03
See application file for complete search history.

(56) References Cited

U.S. PATENT DOCUMENTS

| 4,295,738 A | 10/1981 | Meltz et al. |
| 4,567,769 A | 2/1986 | Barkhoudarian |

(Continued)

FOREIGN PATENT DOCUMENTS

| EP | 1744156 A2 | 1/2007 |
| EP | 2345881 A1 | 7/2011 |

(Continued)

OTHER PUBLICATIONS

Office Action, dated Jan. 30, 2015, regarding U.S. Appl. No. 13/526,698, 32 pages.

(Continued)

*Primary Examiner* — Eric S McCall
(74) *Attorney, Agent, or Firm* — Yee & Associates, P.C.

(57) ABSTRACT

An apparatus comprises an inspection vehicle, a sensor system, a positioning system, a controller, and a support system. The inspection vehicle is configured to move on a surface of an object. The sensor system is associated with the inspection vehicle and is configured to generate information about the object when the inspection vehicle is on the surface of the object. The positioning system is configured to determine a location of the inspection vehicle on the object. The controller is configured to control movement of the inspection vehicle using the positioning system and control operation of the sensor system. The support system is connected to the inspection vehicle and is configured to support the inspection vehicle in response to an undesired release of the inspection vehicle from the surface of the object.

20 Claims, 13 Drawing Sheets

(51) Int. Cl.
*B64F 5/00* (2006.01)
*G01N 29/04* (2006.01)
*G01N 29/44* (2006.01)
*G01N 27/00* (2006.01)
*G01N 29/00* (2006.01)
*G01N 25/72* (2006.01)
*G01N 27/90* (2006.01)
*G01M 17/00* (2006.01)
*G01N 21/95* (2006.01)

(52) U.S. Cl.
CPC .............. *G01N 27/00* (2013.01); *G01N 29/00* (2013.01); *G01N 29/043* (2013.01); *G01N 29/4481* (2013.01); *G01M 17/00* (2013.01); *G01N 21/9515* (2013.01); *G01N 25/72* (2013.01); *G01N 27/90* (2013.01); *G01N 2291/2694* (2013.01)

(56) References Cited

U.S. PATENT DOCUMENTS

| | | | |
|---|---|---|---|
| 5,473,953 | A | 12/1995 | Appel |
| 6,003,377 | A | 12/1999 | Waag et al. |
| 7,369,250 | B2 | 5/2008 | Dubois et al. |
| 7,643,893 | B2 | 1/2010 | Troy et al. |
| 7,743,660 | B2 | 6/2010 | Marsh et al. |
| 7,859,655 | B2 | 12/2010 | Troy et al. |
| 8,044,991 | B2 | 10/2011 | Lea et al. |
| 8,198,617 | B2 | 6/2012 | Georgeson et al. |
| 8,224,485 | B2 | 7/2012 | Unsworth |
| 8,249,832 | B2 | 8/2012 | Motzer et al. |
| 8,279,412 | B2 | 10/2012 | Motzer et al. |
| 8,347,746 | B2 | 1/2013 | Hafenrichter et al. |
| 2003/0043964 | A1 | 3/2003 | Sorenson |
| 2003/0147493 | A1 | 8/2003 | Bueno et al. |
| 2004/0003662 | A1 | 1/2004 | Kenderian et al. |
| 2005/0274188 | A1 | 12/2005 | Cabanis et al. |
| 2006/0055396 | A1 | 3/2006 | Georgeson et al. |
| 2006/0055399 | A1 | 3/2006 | Georgeson et al. |
| 2008/0307886 | A1 | 12/2008 | Marsh et al. |
| 2009/0086014 | A1 | 4/2009 | Lea et al. |
| 2010/0153051 | A1 | 6/2010 | Georgeson et al. |
| 2010/0291599 | A1 | 11/2010 | Tague, Jr. et al. |
| 2011/0178727 | A1 | 7/2011 | Hafenrichter et al. |
| 2012/0221625 | A1 | 8/2012 | Lea et al. |
| 2012/0304774 | A1 | 12/2012 | Ishioka |
| 2012/0320372 | A1 | 12/2012 | Troy et al. |
| 2013/0018525 | A1 | 1/2013 | Jang et al. |

FOREIGN PATENT DOCUMENTS

| | | |
|---|---|---|
| GB | 2057697 | 4/1981 |
| GB | 2491978 | 12/2012 |

OTHER PUBLICATIONS

Office Action, dated Jan. 5, 2015, regarding U.S. Appl. No. 13/527,021, 25 pages.
Office Action, dated Feb. 18, 2015, regarding U.S. Appl. No. 13/596,977, 31 pages.
Final Office Action, dated Oct. 6, 2014, regarding U.S. Appl. No. 13/526,698, 33 pages.
Final Office Action, dated Oct. 22, 2014, regarding U.S. Appl. No. 13/526,853, 28 pages.
Final Office Action, dated Oct. 28, 2014, regarding U.S. Appl. No. 13/527,021, 33 pages.
UK Combined Search and Examination Report, dated Oct. 10, 2012, regarding Application No. GB1210632.4, 6 pages.
Office Action, dated Jun. 3, 2013, regarding U.S. Appl. No. 13/160,238, 17 pages.
Final Office Action, dated Oct. 29, 2013, regarding U.S. Appl. No. 13/160,238
Notice of Allowance, dated Dec. 16, 2013, regarding U.S. Appl. No. 13/160,238, 7 pages.
Bossi et al., "Ultrasound Inspection System for Inspecting a Test Object with Non-Planar Features," U.S. Appl. No. 13/596,977, filed Aug. 28, 2012, 107 pages.
Office Action, dated Apr. 15, 2015, regarding U.S. Appl. No. 13/526,853, 16 pages.
Office Action, dated Apr. 15, 2015, regarding U.S. Appl. No. 13/527,021, 17 pages.
Notice of Allowance, dated Jun. 5, 2015, regarding U.S. Appl. No. 13/527,021, 11 pages.
Office Action, dated Apr. 14, 2015, regarding U.S. Appl. No. 13/526,698, 17 pages.
Notice of Allowance, dated Jul. 7, 2015, regarding U.S. Appl. No. 13/526,698, 9 pages.
Office Action, dated Aug. 14, 2014, regarding U.S. Appl. No. 13/596,977, 40 pages.

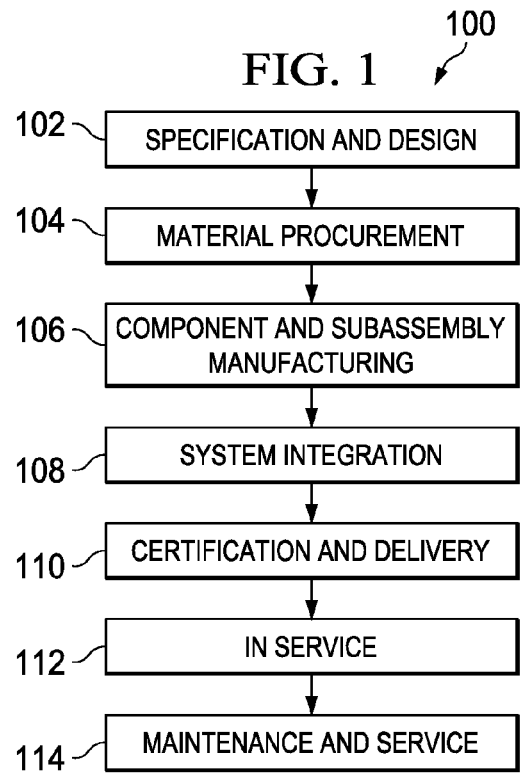
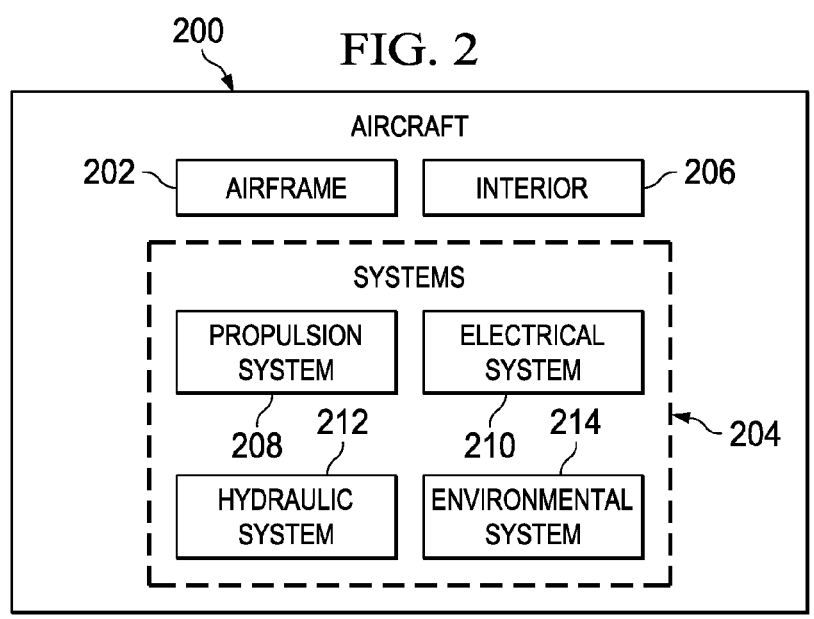

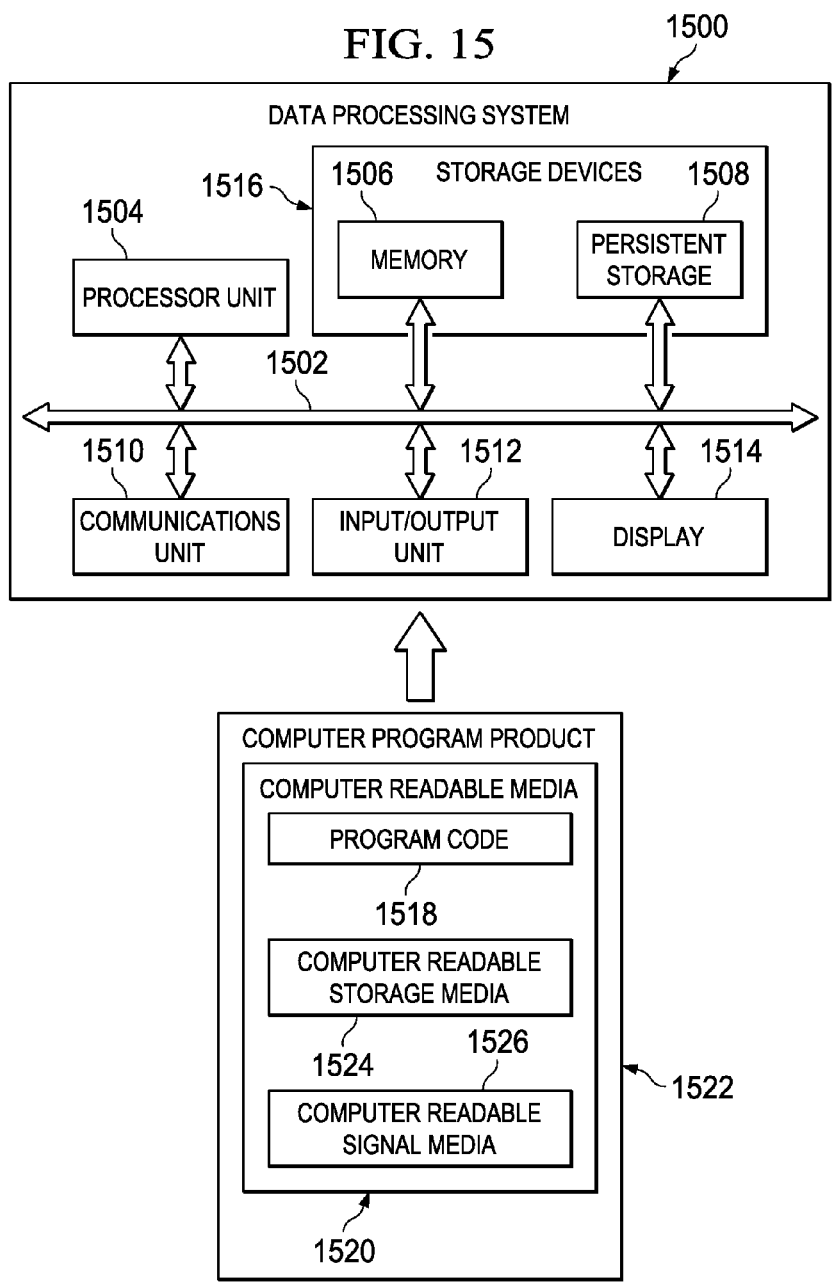

AUTONOMOUS NON-DESTRUCTIVE EVALUATION SYSTEM FOR AIRCRAFT STRUCTURES

This application is a continuation of U.S. application Ser. No. 13/160,238, filed Jun. 14, 2011; status, Allowed.

BACKGROUND INFORMATION

1. Field

The present disclosure relates generally to aircraft structures and, in particular, to inspecting aircraft structures. Still more particularly, the present disclosure relates to a method and apparatus for computer-controlled non-destructive evaluation (NDE) of aircraft structures.

2. Background

Aircraft structures may be examined at different times to determine whether the aircraft structures have desired properties. For example, an aircraft structure may be inspected during manufacturing of the aircraft structure. If the aircraft structure does not have the desired properties, that aircraft structure may be reworked or discarded.

For example, skin panels for an aircraft may be inspected during manufacturing of the skin panels. The inspection may be performed to determine whether undesired inconsistencies are present in the skin panels.

Inspection of aircraft structures also may occur after the aircraft structure has been sent to a customer for use. For example, skin panels on an aircraft may be examined after the aircraft has been in use. This inspection may occur, for example, between flights. In other cases, the inspection may be performed as part of a maintenance operation when the aircraft is taken out of service for maintenance.

Further, the inspection may be performed to determine whether an undesired inconsistency is present in the skin panels on the aircraft. An inconsistency may occur as a result of the stresses in loads placed upon the skin panels during flight, take off, and/or landing. Exposure to the environment also may cause an inconsistency in the skin panels. In some cases, the inconsistency may be an undesired inconsistency. If an undesired inconsistency is found, then the skin panel may be reworked or replaced on the aircraft.

These inspections may be performed using non-destructive evaluation (NDE) tests. A non-destructive evaluation test is a test in which a structure is evaluated without causing undesired changes to the structure. This type of test may be used to evaluate properties of the structure. In particular, this type of test may be used to identify inconsistencies that may be present in a structure. Non-destructive evaluation also may be referred to as non-destructive testing (NDT), non-destructive inspection (NDI), and non-destructive examination (NDE).

The different types of techniques used to perform non-destructive evaluation testing are highly valuable techniques that may save money and time in examining structures because these types of techniques do not permanently change a structure in an undesired manner. Examples of techniques for performing non-destructive evaluation testing include, for example, without limitation, ultrasonic inspection, remote visual inspection, eddy current testing, laser shearography, thermography, magnetic and optical imaging, and other suitable types of testing techniques that do not alter a structure in an undesired manner.

The inspection of aircraft structures on an aircraft is often performed by human operators using handheld devices. For example, a human operator may perform an inspection of an aircraft using a handheld eddy current sensor device to determine whether an inconsistency is present in the skin panel of the aircraft.

In particular, the human operator may need to move the handheld eddy current sensor device along the surface of a skin panel of an aircraft to determine whether the inconsistency is present. The human operator also may need to collect and record information about the inconsistencies. This type of inspection is time consuming.

The amount of time needed to perform an inspection of structures on an aircraft may be reduced by increasing the number of operators performing the inspection of the structures on the aircraft. Although having additional operators to perform inspections may reduce the time needed for inspecting the structures, having more operators increases the cost for inspecting an aircraft.

Thus, it would be illustrative to have a method and apparatus that takes into account one or more of the issues discussed above, as well as possible other issues.

SUMMARY

In one illustrative embodiment, an apparatus comprises an inspection vehicle, a sensor system, a positioning system, a controller, and a support system. The inspection vehicle is configured to move on a surface of an object. The sensor system is associated with the inspection vehicle and is configured to generate information about the object when the inspection vehicle is on the surface of the object. The positioning system is configured to determine a location of the inspection vehicle on the object. The controller is configured to control movement of the inspection vehicle using the positioning system and control operation of the sensor system. The support system is connected to the inspection vehicle and is configured to support the inspection vehicle in response to an undesired release of the inspection vehicle from the surface of the object.

In another illustrative embodiment, a non-destructive evaluation inspection system for an aircraft comprises an inspection vehicle, a sensor system, a support system, a positioning system, and a controller. The inspection vehicle is configured to move on a surface of the aircraft. The sensor system is connected to the inspection vehicle and configured to obtain information about the aircraft when the inspection vehicle is on the surface of the aircraft. The support system comprises a reel, an elongate member, and a number of lines connected to the elongate member and the inspection vehicle. The support system is configured to support the inspection vehicle in response to an undesired release of the inspection vehicle from the surface of the aircraft. The positioning system is configured to determine a location of the inspection vehicle on the aircraft. The controller is configured to control movement of the inspection vehicle based on the location of the inspection vehicle.

In yet another illustrative embodiment, a method for inspecting an object is provided. A location of an inspection vehicle on a surface of an object is determined using a positioning system. Information about the object is generated using a sensor system connected to the inspection vehicle while the inspection vehicle is on the surface of the object. Movement of the inspection vehicle is controlled using a controller. The inspection vehicle is supported in response to an undesired release of the inspection vehicle from the surface of the object using a support system connected to the inspection vehicle.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the disclosure are set forth in the appended claims. The disclosure itself, however, as well as a preferred mode of use, further objectives and advantages thereof, will best be understood by reference to the following detailed description of an illustrative embodiment of the present disclosure when read in conjunction with the accompanying drawings, wherein:

FIG. 1 is an illustration of an aircraft manufacturing and service method in accordance with an illustrative embodiment;

FIG. 2 is an illustration of an aircraft in which an illustrative embodiment may be implemented;

FIG. 15 is an illustration of a data processing system in accordance with an illustrative embodiment.

DETAILED DESCRIPTION

Figure 3:
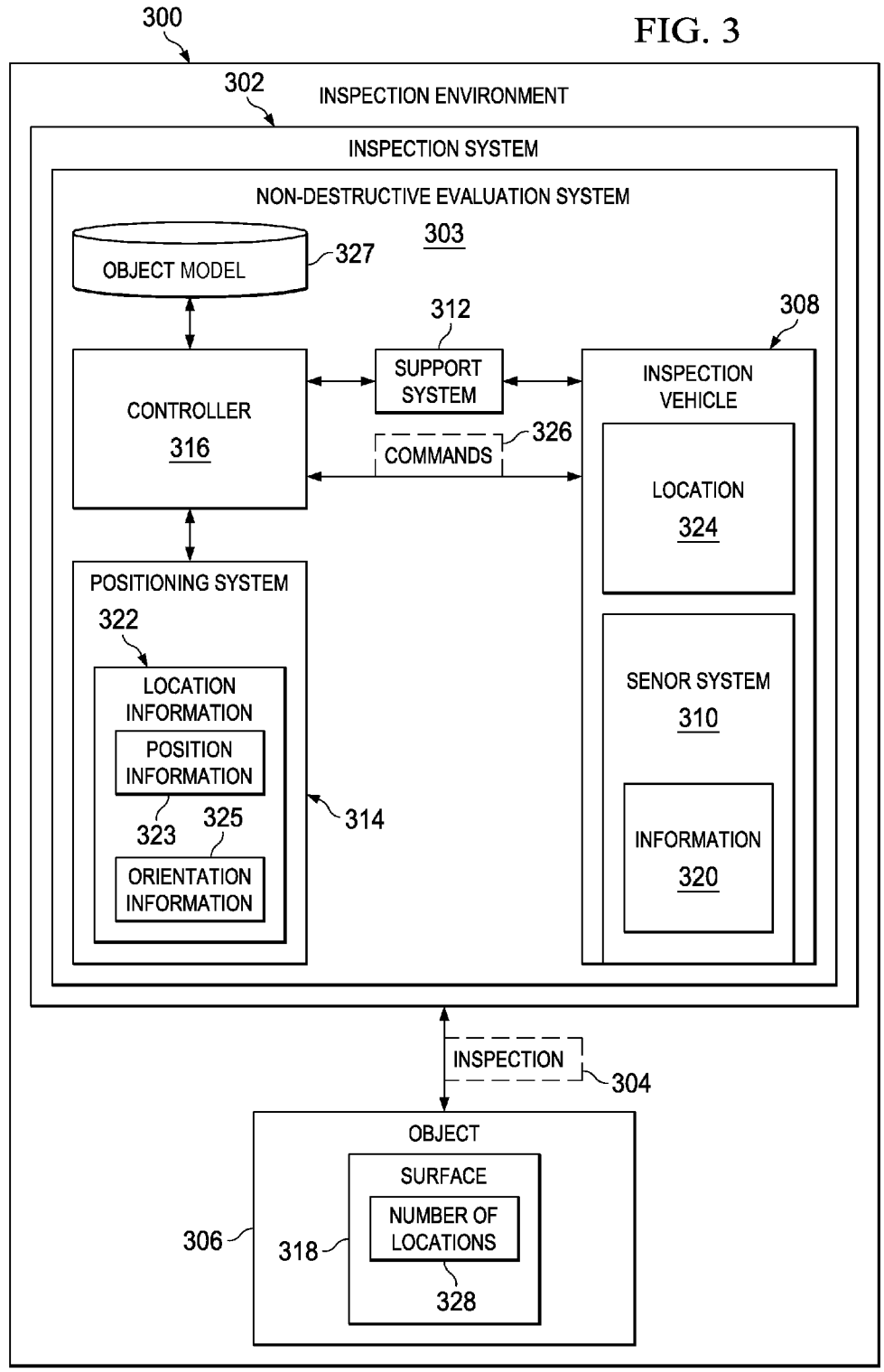
FIG. 3 is an illustration of an inspection environment in accordance with an illustrative embodiment.

Referring more particularly to the drawings, one or more illustrative embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an illustrative embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service 112 by a customer, aircraft 200 in FIG. 2 may be scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, a maintenance facility, a rework facility, and so on.

With reference now to FIG. 2, an illustration of an aircraft is depicted in which an illustrative embodiment may be implemented. In this example, aircraft 200 is produced by aircraft manufacturing and service method 100 in FIG. 1 and may include airframe 202 with plurality of systems 204 and interior 206. Examples of systems 204 include one or more of propulsion system 208, electrical system 210, hydraulic system 212, and environmental system 214. Any number of other systems may be included. Although an aerospace example is shown, different illustrative embodiments may be applied to other industries, such as the automotive industry.

Apparatus and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A, or item A and item B. This example also may include item A, item B, and item C, or item B and item C. In other examples, "at least one of" may be, for example, without limitation, two of item A, one of item B, and ten of item C; four of item B and seven of item C; and other suitable combinations.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments may be one or more apparatus embodiments.

A number of apparatus embodiments, method embodiments, or a combination thereof may be utilized while aircraft 200 is in service 112 and/or during maintenance and service 114 in FIG. 1. The use of a number of the different illustrative embodiments may substantially expedite the assembly of and/or reduce the cost of aircraft 200.

In particular, one or more of the different illustrative embodiments may be used to perform non-destructive evaluation (NDE) testing using one or more illustrative embodiments to inspect structures, such as those in airframe 202 of aircraft 200.

The different illustrative embodiments recognize and take into account a number of different considerations. For example, the different illustrative embodiments recognize and take into account that when human operators perform inspections of aircraft using non-destructive evaluation testing, the human operators may collect data during the testing.

This data may be used by the human operators to determine whether an inconsistency is present in the structure being tested.

Further, the different illustrative embodiments recognize and take into account that inconsistencies may be detected during testing that are undesired inconsistencies. The different illustrative embodiments recognize and take into account that it may be desirable to save information about inconsistencies found in different locations on an aircraft to generate a history for those locations.

The different illustrative embodiments recognize and take into account that performing additional testing at times other than during scheduled maintenance may be desirable for locations in which inconsistencies have been detected. For example, additional testing may be performed for inconsistencies that have been detected, but that do not meet the criteria for requiring maintenance or further testing. The different illustrative embodiments recognize and take into account that without recording information generated from prior inspections, scheduling additional inspections at other times may be infeasible.

The different illustrative embodiments also recognize and take into account that non-destructive evaluation testing may be performed in an automated manner. For example, a vehicle with a non-destructive testing device may be placed on an aircraft and moved along the surface of the aircraft to perform the inspection. The information generated by the vehicle from performing the tests for the inspection may be analyzed and stored for future use.

The different illustrative embodiments recognize and take into account, however, that inspection vehicles may have more difficulties inspecting different portions of an aircraft than desired. For example, curved surfaces of the aircraft may make it more difficult for an inspection vehicle to move along the surface in those areas without slipping on the aircraft and/or falling off the aircraft.

Further, the different illustrative embodiments recognize and take into account that in addition to obtaining information from non-destructive evaluation testing, obtaining information identifying the locations at which the testing is performed may be desirable. The different illustrative embodiments recognize and take into account that a vehicle may include one or more rotational encoders associated with the wheels of the vehicle. The distance at which the vehicle travels may be recorded along with the information gathered from non-destructive evaluation testing.

The different illustrative embodiments recognize and take into account, however, that the information about the location at which testing is performed is based on offsets from a starting location. The different illustrative embodiments also recognize and take into account that inaccurate identification of the starting point may cause inaccurate identification of the location at which the testing is performed.

In some cases, even with an accurate identification of a starting point for the inspection in a system that uses rotational encoders, the wheels or tracks of the inspection vehicle may slip. As a result, the identification of the location of the inspection vehicle during the performance of non-destructive evaluation testing may not be as accurate as desired.

Additionally, the different illustrative embodiments recognize and take into account that correlating the location of the testing with different structures on the aircraft may be more difficult than desired. For example, with currently available methods for non-destructive evaluation testing, registering images and/or scans of a structure generated during the testing with a computer model of the structure may be more difficult than desired.

Thus, the different illustrative embodiments provide a method and apparatus for non-destructive evaluation testing. One or more of the different illustrative embodiments may be performed in a manner to provide autonomous non-destructive evaluation of structures for an aircraft. In other words, the non-destructive evaluation testing may be performed without user intervention or input during the testing of the structure.

In one illustrative embodiment, an apparatus comprises an inspection vehicle, a sensor system, a positioning system, a controller, and a support system. The inspection vehicle is configured to move on a surface of an object. The sensor system is associated with the inspection vehicle and is configured to generate information about the object when the inspection vehicle is on the surface of the object. The positioning system is configured to determine a location of the inspection vehicle on the object. The controller is configured to control movement of the inspection vehicle using the positioning system and control operation of the sensor system. The support system is connected to the inspection vehicle and is configured to support the inspection vehicle in response to an undesired release of the inspection vehicle from the surface of the object.

With reference now to FIG. 3, an illustration of an inspection environment is depicted in accordance with an illustrative embodiment. Inspection environment 300 is an example of an inspection environment that may be used to inspect aircraft 200 in FIG. 2.

This inspection environment may be used at different times during aircraft manufacturing and service method 100. The inspection may occur during, for example, without limitation, component and subassembly manufacturing 106, certification and delivery 110, and/or maintenance and service 114.

Inspection system 302 in inspection environment 300 may be used to perform inspection 304 of object 306. As depicted, inspection system 302 is non-destructive evaluation system 303. Object 306 may be selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, roadway, a building, and/or some other suitable type of object.

In these illustrative examples, inspection system 302 comprises inspection vehicle 308, sensor system 310, support system 312, positioning system 314, and controller 316. Inspection vehicle 308 is configured to move on surface 318 of object 306. For example, inspection vehicle 308 may have a size that is suitable for moving on surface 318 of object 306 in a desirable manner.

Sensor system 310 is associated with inspection vehicle 308 in these depicted examples. The association is a physical association in these examples. A first component, such as non-destructive evaluation system 310, may be considered to be associated with a second component, such as inspection vehicle 308, by being secured to the second component, bonded to the second component, welded to the second component, fastened to the second component, and/or connected to the second component in some other suitable manner. The first component also may be connected to the second component using a third component. The first component also may be considered to be associated with the second component by being formed as part of and/or an extension of the second component.

In these illustrative examples, sensor system 310 may comprise a number of sensors. For example, sensor system 310 may comprise at least one of a camera, an infrared sensor, an ultrasound sensor, an eddy current testing sensor, a thermometer, an interferometer, an optical sensor, a laser system, and other suitable types of sensors.

Sensor system 310 is configured to generate information 320 about object 306. Information 320 may be generated while inspection vehicle 308 is on surface 318 of object 306. Information 320 may be used in determining whether an inconsistency is present in object 306.

Support system 312 is connected to inspection vehicle 308. Support system 312 may include, for example, cables that connect inspection vehicle 308 to a structure. In other words, support system 312 may tether inspection vehicle 308 to the structure.

Support system 312 may include a number of different lines. For example, support system 312 may include tether cables and/or tension cables to lift inspection vehicle 308 and/or restrict movement of inspection vehicle 308. Further, support system 312 also may include lines that carry electrical power, data, and/or fluid for inspection vehicle 308.

In these illustrative examples, support system 312 is configured to support inspection vehicle 308 as inspection 304 is being performed. For example, support system 312 may support inspection vehicle 308 in response to an undesired release of inspection vehicle 308 from surface 318 of object 306. This undesired release may be, for example, inspection vehicle 308 slipping from surface 318, falling off of surface 318, sliding on surface 318, and/or having some other type of undesired motion relative to surface 318 of surface 318.

Further, support system 312 may limit the type of and/or range of motion of inspection vehicle 308. In this manner, the possibility of undesired and/or unplanned movement of inspection vehicle 308 may be reduced.

In these illustrative examples, positioning system 314 may be used in determining a location of inspection vehicle 308. In particular, positioning system 314 may be used in determining location 324 of inspection vehicle 308 on object 306 with respect to a coordinate system for object 306. Location 324 of inspection vehicle 308 includes a position and/or orientation of inspection vehicle 308. The position may be defined using the coordinate system for object 306. The orientation may be defined using a number of angles for inspection vehicle 306 relative to a number of axes for object 306.

For example, positioning system 314 generates location information 322. Location information 322 may include position information 323 and orientation information 325. Position information 323 may be used in determining the position of inspection vehicle 308 relative to object 306. Orientation information 325 may be used in determining the orientation of inspection vehicle 308 relative to object 306.

In these illustrative examples, location information 322 may take various forms. For example, location information 322 may comprise a measured position and/or orientation for inspection vehicle 308 relative to object 306. In other illustrative examples, location information 322 may be information that may be used to calculate location 324 of inspection vehicle 308.

In these illustrative examples, positioning system 314 may comprise a motion capture positioning system, an inertial navigation positioning system, and/or other suitable types of positioning systems. Of course, any type of positioning system configured to generate location information 322 may be used in positioning system 314.

Location information 322 is sent to controller 316. Location information 322 may be sent continuously such that controller 316 has access to the most current and up to date location information for inspection vehicle 308. In some illustrative examples, location information 322 may be sent to controller 322 periodically and/or in response to some event.

Controller 316 comprises hardware and may include software in these depicted examples. Controller 316 may use location information 322 and object model 327 of object 306 to determine location 324 of inspection vehicle 308 with respect to the coordinate system for object 306. Object model 327 may be a design for object 306, such as, for example, a three-dimensional computer-aided design (CAD) model. Further, object model 327 includes coordinates for a coordinate system for object 306.

Further, controller 316 may use location information 322 to correlate information 320 generated by sensor system 310 with the coordinate system for object 306. As one illustrative example, images generated by sensor system 310 may be registered with object model 327 of object 306.

In this manner, information 320 may be aligned with object model 327 such that a location at which an inconsistency is identified may be more readily identifiable. Further, with these images being registered with object model 327, evaluation of information 320 generated over time may be performed more quickly and/or efficiently as compared to when the images are not registered with object model 327.

Controller 316 is configured to control the movement of inspection vehicle 308 and the operation of sensor system 310 for performing inspection 304. For example, controller 316 uses location information 322 generated by positioning system 314 to guide inspection vehicle 308 towards and/or to maintain a desired position and/or desired orientation for inspection vehicle 308 relative to object 306.

As one illustrative example, controller 316 sends commands 326 to cause inspection vehicle 308 to move on surface 318 of object 306 to perform inspection 304 of object 306. In particular, inspection vehicle 308 may move to number of locations 328 to perform inspection 304. Commands 326 sent by controller 316 may be based on location 324 determined for inspection vehicle 308.

With inspection system 302, inspection vehicle 308 may be selected as one that may be less complex and/or expensive than other inspection vehicles. For example, inspection vehicle 308 may be selected as one that may be lower in cost and complexity.

For example, inspection vehicle 308 does not need a computer system or other controller that includes artificial intelligence, neural-networks, or other types of programs. Instead, inspection vehicle 308 may merely receive commands 326 from controller 316 to move to number of locations 328 that have been selected for inspection 304 at a rate and in a direction specified by controller 316 in commands 326. Also, with the use of controller 316, controller 316 may control other inspection vehicles in addition to inspection vehicle 308 at the same time or at different times.

The different components in inspection system 302 may allow for easier or quicker set ups of inspection system 302 to perform inspections on different objects. Further, inspection system 302 also may allow for use of inspection vehicles that have a size and/or configuration that may make inspecting object 306 easier. This type of configuration may be useful with objects, such as aircraft that may have locations with areas that are difficult for human access.

With the use of positioning system 314 and controller 316, the planning of tests for inspection, and the guidance of inspection vehicle 308 may be performed by controller 316. In this manner, inspection vehicle 308 does not need the intelligence or capability to perform its own planning for performing inspection 304. This planning may include scheduling times at which testing is to be performed using sensor system 310, planning movement to number of locations 328, and/or other types of planning.

The illustration of inspection environment 300 in FIG. 3 is not meant to imply physical or architectural limitations to the manner in which an illustrative embodiment may be implemented. Other components in addition to, and/or in place of, the ones illustrated may be used. Some components may be unnecessary. Also, the blocks are presented to illustrate some functional components. One or more of these blocks may be combined and/or divided into different blocks when implemented in an illustrative embodiment.

For example, inspection system 302 may have one or more additional inspection vehicles in addition to inspection vehicle 308. These additional inspection vehicles may be controlled by additional controllers, positioning systems, and/or support systems. In some illustrative examples, inspection by these additional inspection vehicles may be controlled using controller 316 and positioning system 314.

Figure 4:
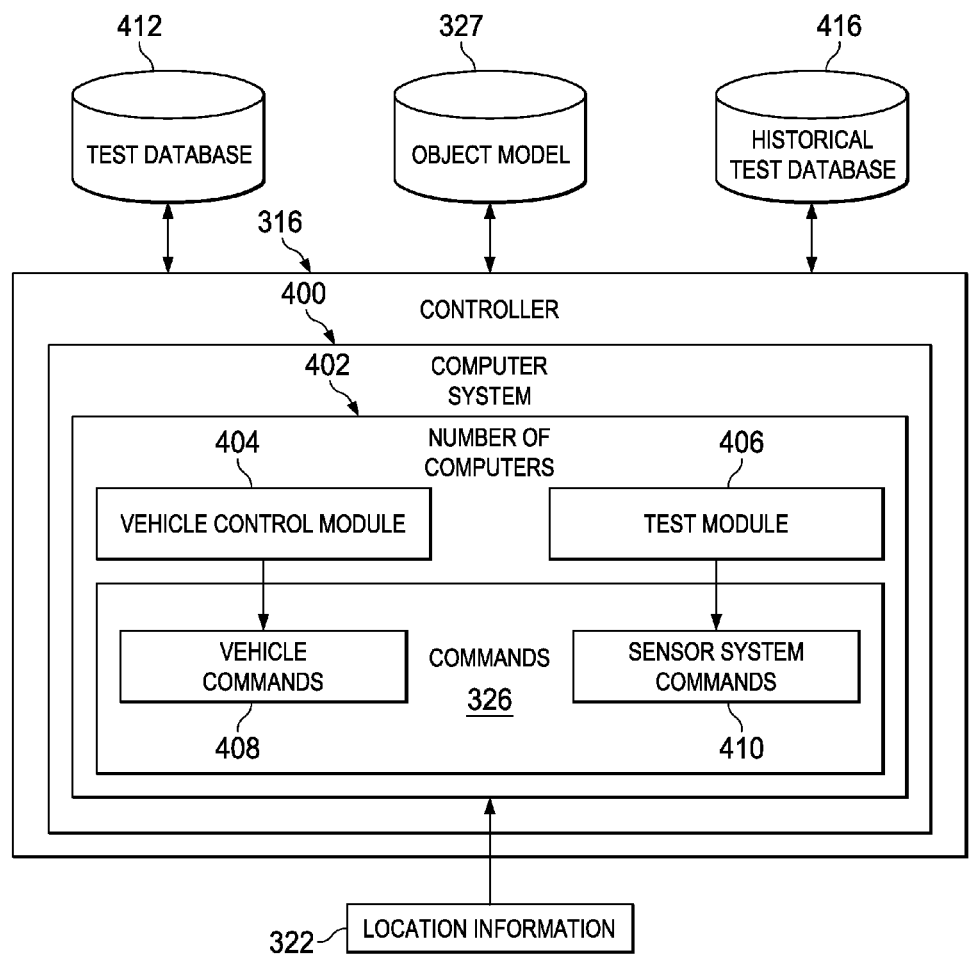
FIG. 4 is an illustration of a controller in accordance with an illustrative embodiment.

With reference now to FIG. 4, an illustration of a controller is depicted in accordance with an illustrative embodiment. In this illustrative example, components for controller 316 are illustrated.

Controller 316 comprises computer system 400. Computer system 400 includes number of computers 402. When more than one computer is present in number of computers 402, those computers may be in communication with each other within computer system 400.

In these illustrative examples, controller 316 includes vehicle control module 404 and test module 406 in computer system 400. These modules may be implemented using hardware, software, or a combination of the two.

Vehicle control module 404 is configured to generate vehicle commands 408 and send vehicle commands 408 to inspection vehicle 308 in FIG. 3. Test module 406 is configured to generate sensor system commands 410 and send testing commands 410 to inspection vehicle 308.

In these illustrative examples, vehicle commands 408 and sensor system commands 410 are examples of the types of commands 326 that may be generated by controller 316. Vehicle commands 408 are commands used to control the movement of inspection vehicle 308. Sensor system commands 410 are commands used to control the operation of sensor system 310.

Vehicle commands 408 and sensor system commands 410 may take different forms depending on the particular implementation. For example, vehicle commands 408 may be commands, such as turn five degrees, move five feet forward, stop, and other similar types of commands. Sensor system commands 410 may include commands as to when to perform scans, what information to return, and other suitable types of commands.

In these illustrative examples, the generation of commands 326 is performed using location information 322 sent to controller 316 by positioning system 314. In generating commands 326, test database 412 is used by controller 316 to identify a particular test to perform on object 306. In identifying a test, test database 412 includes, for example, the types of tests to be performed, the locations where the tests are to be performed, when a test is to be performed, and other suitable types of information.

Object model 327 is used to generate commands 326 to move inspection vehicle 308 to number of locations 328 to perform inspection 304 of object 306 in FIG. 3. Location information 322 may be used to determine location 324 of inspection vehicle 308 with respect to the coordinate system for object 306 in object model 327. With this correlation of coordinates, vehicle commands 408 may be generated to move inspection vehicle 308 to coordinates identified for number of locations 328 in FIG. 3.

Additionally, location information 322 also may be used by test module 406 to generate sensor system commands 410. These commands are generated to cause sensor system 310 to generate information 320 at number of locations 328 based on knowing location 324 of inspection vehicle 308 relative to object 306 with respect to the coordinate system for object 306 in FIG. 3.

Further, location information 322 may be used with information 320 to register information 320 using a common frame of reference for object 306. This common frame of reference may be, for example, a coordinate system for object model 327. In this manner, coordinates for information 320 may be aligned with coordinates for object model 327. Registering information 320 using the coordinate system for object model 327 may allow analysis of information 320, maintenance for object 306, identifying locations on object 306 having inconsistencies, and/or other operations to be performed more easily and efficiently as compared to performing these operations without registering information 320.

In some cases, depending on the manner in which support system 312 is implemented, vehicle control module 404 also may generate commands 326 to operate support system 312. For example, if support system 312 includes a motor, commands 326 may be generated and sent to support system 312 to operate the motor. Additionally, commands 326 may include signals to activate a brake if a brake system is present in support system 312.

Information 320 may be received by test module 406 in these illustrative examples. Information 320 may be saved in historical test database 416. Information 320 may be associated number of locations 328 for which information 320 was generated. In these illustrative examples, test module 406 may receive the current position and orientation of inspection vehicle 308 through location information 322 received from positioning system 314.

In this manner, information about locations in which inconsistencies are present, but not considered to be undesired inconsistencies may be made. With the association of coordinates identifying where the information was generated for these inconsistencies with the information, planning of additional inspections to test these locations may be made. Further, a progression or non-progression of the inconsistencies also may be identified over time. This analysis may be used to determine whether other actions may be needed.

Figure 5:
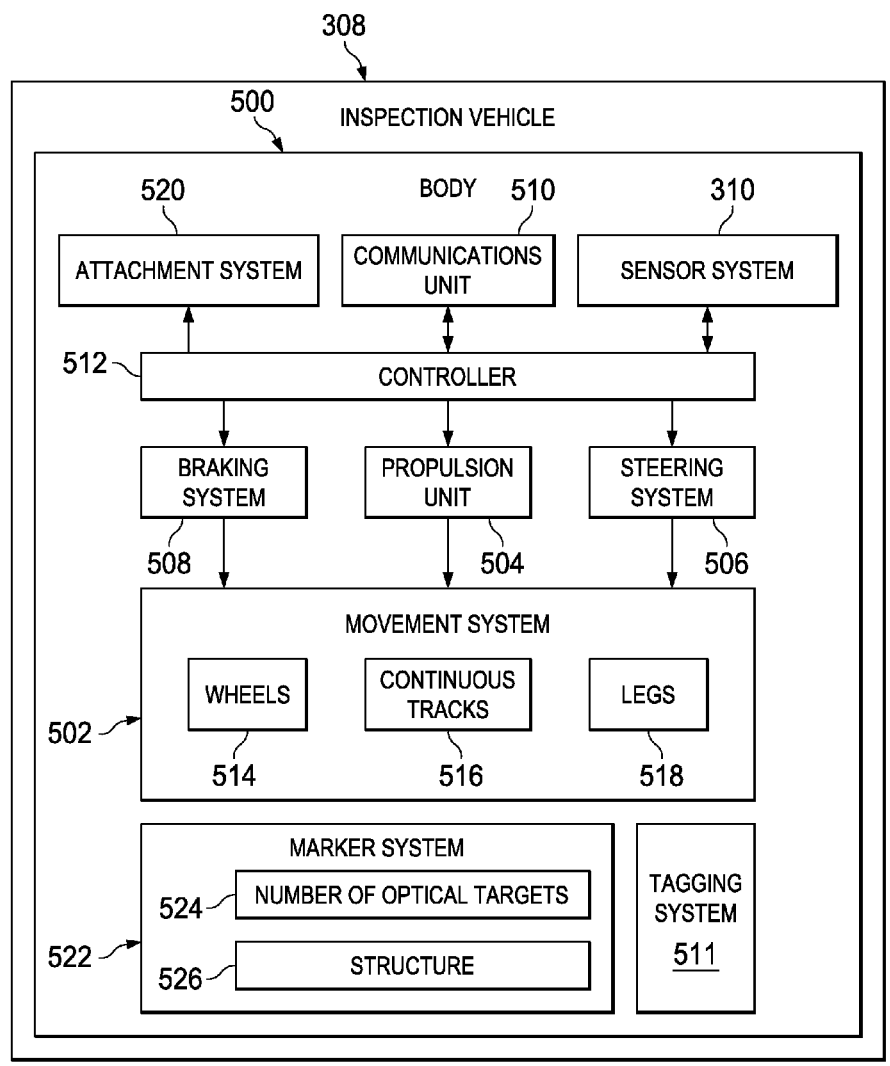
FIG. 5 is an illustration of components for an inspection vehicle in accordance with an illustrative embodiment.

With reference now to FIG. 5, an illustration of components for an inspection vehicle is depicted in accordance with an illustrative embodiment. In this depicted example, examples of components that may be present in inspection vehicle 308 are depicted. The different components for inspection vehicle 308 illustrated in FIG. 5 may be implemented using various components that are currently available for use in vehicles.

As illustrated, inspection vehicle 308 includes body 500, movement system 502, propulsion unit 504, steering system 506, braking system 508, communications unit 510, sensor system 310, and tagging system 511.

Body 500 provides a structure that other components in inspection vehicle 308 may be connected to in these examples. Body 500 may be, for example, without limitation, a frame, a uni-body, or some other suitable type of body.

Movement system 502 comprises components configured to provide movement of inspection vehicle 308. For example, movement system 502 may comprise at least one of wheels 514, continuous tracks 516, legs 518, and other suitable types of movement mechanisms.

Propulsion unit 504 is configured to cause movement by movement system 502. In other words, propulsion unit 504 generates mechanical energy for movement system 502. Propulsion unit 504 may be, for example, an electrical motor.

Steering system 506 is configured to control movement system 502 in different directions. Braking system 508 is used to slow and/or halt movement of movement system 502. Steering system 506 may change the direction in which movement system 502 moves inspection vehicle 308.

Communications unit 510 is configured to allow for the reception of commands and the transmission of information. In these illustrative examples, communications unit 510 may be a wireless communications unit. In other illustrative examples, communications may be provided through a physical connection. With a physical connection, communications unit 510 may be, for example, a network interface card, a modem, or some other suitable type of communications unit.

Controller 512 is configured to receive commands 326 in FIG. 3. In response to these commands, controller 512 controls the operations of movement system 502, propulsion unit 504, steering system 506, and braking system 508. In these illustrative examples, controller 512 may be implemented using a processor, an application specific integration circuit, or some other type of circuit system.

In addition to these components, attachment system 520 may be present in some illustrative examples. Attachment system 520 may aide in attaching inspection vehicle 308 to surface 318 of object 306. In this manner, inspection vehicle 308 may be able to move on inclined, vertical, and/or inverted surfaces without slipping. As a result, additional areas of object 306 may be reachable when using attachment system 520 as compared to when attachment system 520 is absent for inspection vehicle 308.

In these illustrative examples, attachment system 520 may take a number of different forms depending on the implementation. For example, attachment system 520 may include at least one of a suction cup system, a pressure differential system, a magnetic system, and some other suitable type of system for attaching inspection vehicle 308 to surface 318 of object 306 in FIG. 3. A pressure differential system may be any system configured to generate a pressure differential on surface 318 of object 306. A vacuum system is an example of one type of pressure differential system.

Also, depending on the type of system used in positioning system 314, inspection vehicle 308 also may include marker system 522. Marker system 522 is associated with body 500. Marker system 522 is configured to allow positioning system 314 to determine location 324 of inspection vehicle 308. A single marker may be used to determine a position of inspection vehicle 308. Multiple markers may be used to also determine an orientation of inspection vehicle 308.

In these illustrative examples, marker system 522 includes number of optical targets 524. Number of optical targets 524 may be associated with body 500. In these illustrative examples, number of optical targets 524 may take different forms. For example, an optical target in number of optical targets 524 may be selected from one of a light-emitting diode, retro-reflective marker, paint, tape, and other suitable types of markers.

Number of optical targets 524 is used by positioning system 314 to determine a location of inspection vehicle 308. Depending on the particular implementation, number of optical targets 524 may be mounted on structure 526 connected to inspection vehicle 308. Marker system 522 may be considered to be part of positioning system 314 in some illustrative examples.

Sensor system 310 is illustrated as being associated with inspection vehicle 308 in this particular example. Sensor system 310 may be integrated as part of inspection vehicle 308, connected to inspection vehicle 308, and/or removably connected to inspection vehicle 308, depending on the particular implementation. In some cases, when sensor system 310 is removably connected to body 500 of inspection vehicle 308, this system may be considered a separate component from inspection vehicle 308.

Tagging system 511 is configured to allow locations of interest on object 308 to be tagged. Locations of interest may include, for example, locations at which inconsistencies have been detected. Tagging a location may comprise forming some type of visual indication for the location. For example, tagging a location may include at least one of spraying paint at the location, applying ink to the location, applying a sticker to the location, marking the location with a chalk, and other suitable types of physical tagging operations.

In some illustrative examples, virtual tags also may be added that may be associated with object model 327, test database 412, and/or other non-physical representations.

Figure 6:
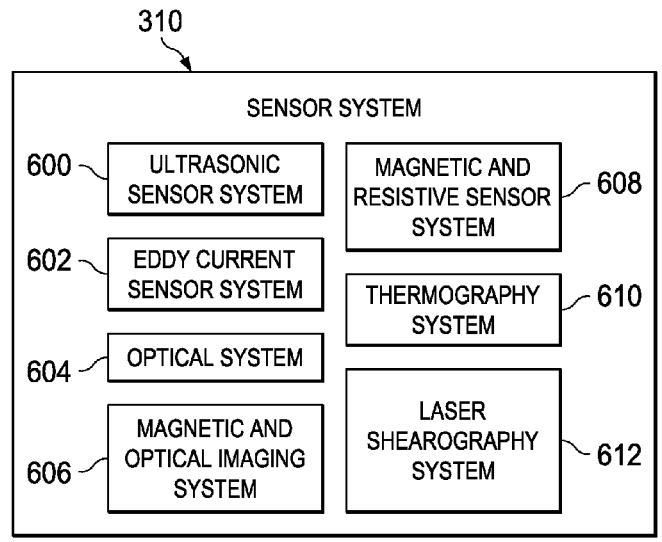
FIG. 6 is an illustration of a non-destructive evaluation system in accordance with an illustrative embodiment.

With reference now to FIG. 6, an illustration of a sensor system is depicted in accordance with an illustrative embodiment. In this illustrative example, components are depicted for sensor system 310. The different types of sensor systems in sensor system 310 may be implemented using currently available non-destructive evaluation systems.

As depicted, sensor system 310 may include at least one of ultrasonic sensor system 600, eddy current sensor system 602, optical system 604, magnetic and optical imaging system 606, magnetic and resistive sensor system 608, thermography system 610, laser shearography system 612, and other suitable types of non-destructive evaluation systems.

Ultrasonic sensor system 600 may include an array of transducers that are configured to send signals into object 306 and detect responses from those signals. Eddy current sensor system 602 may include an array of probes that generates a magnetic field that induces eddy currents in an object and detects changes in the eddy currents based on the structure of object 306.

Optical system 604 may provide for visual inspections. Images may be generated by optical system 604 to characterize object 306. Of course, in other illustrative examples, sensor system 310 may include an imaging system in addition to, and/or in place of, optical system 604.

Magnetic and optical imaging system 606 is configured to use garnet crystals to provide a two-dimensional image of the electromagnetic field changes caused by eddy currents in object 306. Magnetic and resistive sensor system 608 is configured to detect changes in the flow of current in object 306 in response to applying a magnetic field.

Further, thermography system 610 is configured to generate infrared images of object 306 that are used to detect inconsistencies in object 306. Laser shearography system 612 may be used to analyze strain measurements generated in response to an applied stress to object 306.

Figure 7:
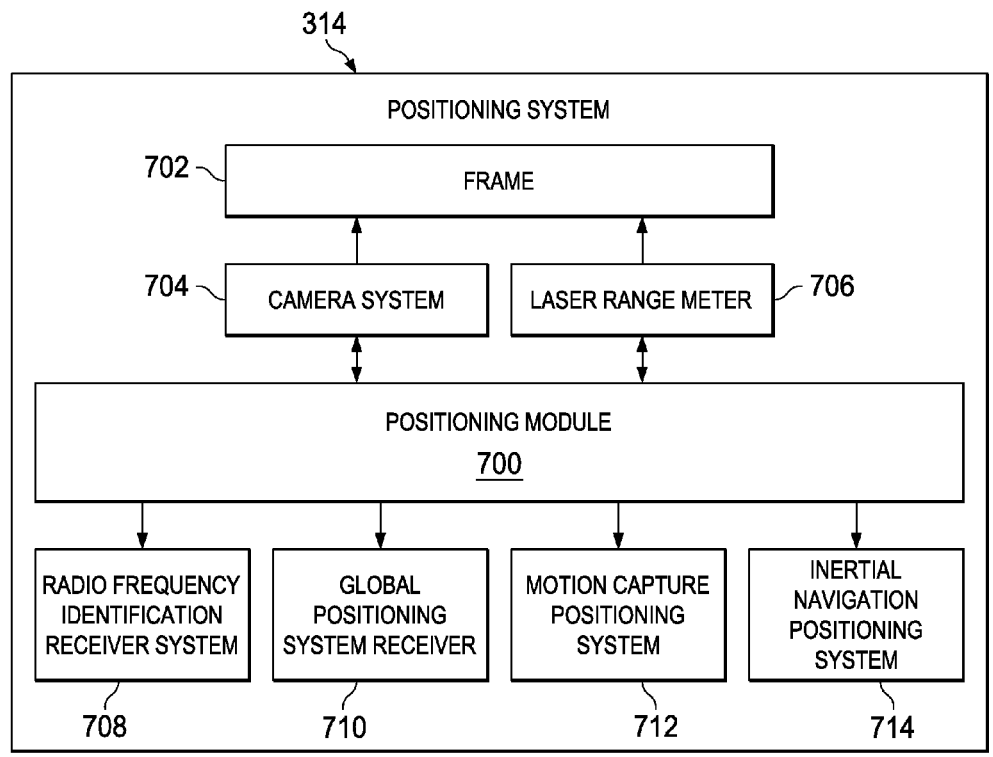
FIG. 7 is an illustration of a positioning system in accordance with an illustrative embodiment.

With reference now to FIG. 7, an illustration of a positioning system is depicted in accordance with an illustrative embodiment. In this illustrative example, components for positioning system 314 are depicted.

Positioning system 314 may include, for example, positioning module 700, frame 702, camera system 704, and laser range meter 706. Camera system 704 and laser range meter 706 may be implemented using currently available camera systems and laser range meter devices. Frame 702 is a structure in which different components in positioning system 314 may be mounted on or connected to in these examples. Frame 702 may be, for example, without limitation, a stand, a ceiling mount, or some other suitable type of structure.

Camera system 704 is configured to generate images. Camera system 704 may be implemented using any camera configured to generate images. For example, camera system 704 may include at least one of visible light cameras, infrared light cameras, and other suitable types of cameras.

Laser range meter 706 is configured to measure distances to a target, such as inspection vehicle 308. Laser range meter 706 may have a laser and a unit configured to compute distances based on the laser light detected in response to a laser beam bouncing off of a target.

The images and distances along with a position and orientation of camera system 704 and laser range meter 706 may be used to generate location information 322 by positioning module 700. In other illustrative examples, this information may be location information 322 and sent back to controller 316, which then determines location 324 of inspection vehicle 308.

Positioning module 700 also may change the orientation of camera system 704, laser range meter 706, or both. The change in orientation of these components may be performed to track inspection vehicle 308 as inspection vehicle 308 moves on object 306 in FIG. 3. The change in orientation of camera system 704, laser range meter 706, or both may be controlled by controller 316, positioning module 700, or a combination of the two. For example, controller 316 may identify targets to be tracked from images generated by camera system 704.

In other illustrative examples, positioning system 314 may take other forms. For example, positioning system 314 may include radio frequency identification receiver system 708, global positioning system receiver 710, and/or other types of positioning systems in addition to, and/or in place of, camera system 704 and laser range meter 706. In some illustrative examples, positioning system 314 may include motion capture positioning systems 712 and/or inertial navigation positioning systems 714.

With radio frequency identification receiver system 708, radio frequency identification receiver systems may be positioned on frame 702. Radio frequency identification tags may be associated with inspection vehicle 308. Based on the strength and direction at which signals are received from these tags, positioning module 700 may determine a position and orientation of inspection vehicle 308.

With global positioning system receiver 710, some components of positioning system 314 may actually be located on inspection vehicle 308 rather than as a separate component. Global positioning system receiver 710 may generate coordinate information about a location of inspection vehicle 308. This coordinate information may be in latitude, longitude, and elevation.

This coordinate information may be translated into a coordinate system for object 306 in these illustrative examples. This translation may be performed by positioning module 700 and/or from one coordinate system to another coordinate system by controller 316.

With motion capture positioning system 712, the positions of retro-reflective markers are tracked using two or more integrated illuminators. When three or more retro-reflective markers are grouped in a known configuration and placed on inspection vehicle 308, the positions of the three or more markers and their known relative offset positions can be used to determine the position and orientation of inspection vehicle 308.

As inspection vehicle 308 is moved within the field-of-view of the two or more cameras, marker positions are continuously tracked and used to generate substantially real-time position and orientation measurements of inspection vehicle 308. Using this process, inspection vehicle 308 can be tracked while moving on surface 318 of object 306 during inspection 304 in FIG. 3.

In addition, if three or more makers are placed on surface 318 of object 306, the position and orientation of inspection vehicle 308 relative to surface 318 may be obtained. Using motion capture positioning system 712, multiple inspection vehicles 308, may be tracked simultaneously. Motion capture positioning system 712 may be controlled using positioning module 700.

Inertial navigation system 714 is configured to process acceleration and rotational rate data from an inertial measurement unit (IMU) sensor. This processing may be performed to determine a position and orientation of inspection vehicle 308 relative to a starting location.

The illustration of radio frequency identification receiver system 708, global positioning system receiver 710, and motion capture positioning system 712 are only examples of positioning systems. For example, other types of positioning systems may be used in addition to, and/or in place of, camera system 704 and laser range meter 706.

In these illustrative examples, other types of systems also may be used in place of, and/or in addition to, these systems depending on the particular implementation. For example, positioning system 314 may include systems, such as a camera tracking system, a laser tracking system, and/or some other suitable type of positioning system. Additionally, these systems may be implemented using currently available systems to determine the position and orientation of objects.

Figure 8:
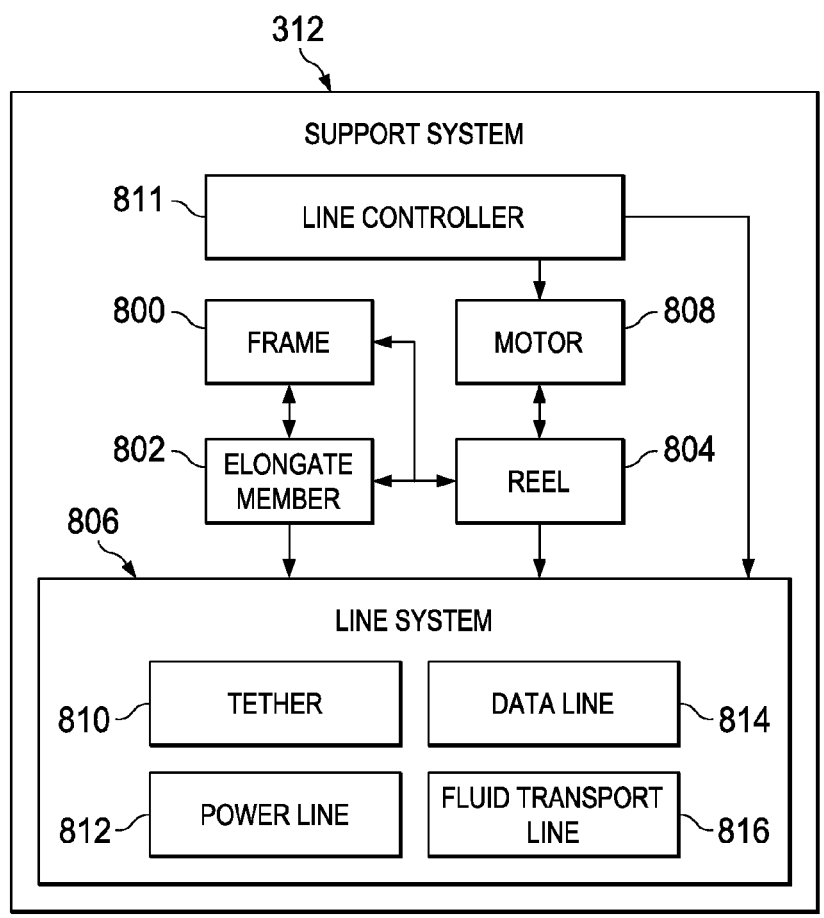
FIG. 8 is an illustration of a support system in accordance with an illustrative embodiment.

With reference now to FIG. 8, an illustration of a support system is depicted in accordance with an illustrative embodiment. In this illustrative example, support system 312 includes frame 800.

Elongate member 802 may be attached to frame 800. Additionally, reel 804 may be connected to elongate member 802 and/or frame 800. Line system 806 may be connected to reel 804 and elongate member 802. Line system 806 connects support system 312 to inspection vehicle 308.

Elongate member 802 may take various forms. For example, elongate member 802 may be a rod, a boom, or some other suitable type of elongate member. In some cases, elongate member 802 also may be flexible.

In these illustrative examples, line system 806 is one or more lines. Line system 806 may restrict or aide in managing movement of inspection vehicle 308.

For example, reel 804 may be a tensionable reel and may include a brake unit. Reel 804 may be configured to hold a line in line system 806 and supply a level of tension to the line. Further, reel 804 may reduce the slack in line system 806. A tensionable reel is a reel in which the reel is biased to rotate in a direction to take up slack that may occur in line system 806. The brake unit may halt and/or reduce the rate at which the line being held by reel 804 is allowed to be drawn out from the reel.

As a result, support system 312 may reduce the possibility of an undesired release of inspection vehicle 308 from surface 318 of object 306 causing undesired effects to inspection vehicle 308, object 306, and/or other objects and/or personnel in inspection environment 300. An undesired release of inspection vehicle 308 from surface 318 may be, for example, a slippage, falling, or sliding of inspection vehicle 308 when inspection vehicle 308 is on surface 318 of object 306. In this manner, support system 312 may provide the equivalent of a safety net for inspection vehicle 308.

Motor 808 may be used to turn reel 804 if a tensionable reel is not present. In particular, motor 808 may turn reel 804 in a manner that increases tension or reduces slack in line system 806. Reel 804 may increase tension in line system 806 in a manner that may reduce or halt movement of inspection vehicle 308. Further, reel 804 also may be used in lifting and/or moving inspection vehicle 308 in some illustrative examples.

Additionally, in these illustrative examples, support system 312 may include line controller 811. Line controller 811 is configured to control a set of lines in line system 806 connected to line controller 811 to perform at least one of supporting inspection vehicle 308 in response to an undesired release of inspection vehicle 308 from surface 318 of object 306, slowing the movement of inspection vehicle 308, halting the movement of inspection vehicle 308, supporting inspection vehicle 308 as inspection vehicles 308 moves on surface 318 of object 306, lifting inspection vehicle 308, and other suitable operations.

Further, line controller 811 also may be configured to control a set of lines in line system 806 in response to a number of commands received from controller 316. Line controller 811 also may control motor 808 and/or reel 804 to control line system 806. Of course, in other illustrative examples, line controller 811 may not be present in support system 312.

In these illustrative examples, line system 806 includes tether 810, power line 812, data line 814, and fluid transport line 816. Of course, line system 806 may include other types of lines depending on the implementation. Tether 810 provides support for controlling movement of inspection vehicle 308. Power line 812 may provide power to inspection vehicle 308. Data line 814 may provide a communications link to inspection vehicle 308. Fluid transport line 816 may carry fluids, such as water. When ultrasonic sensor system 600 is present in inspection vehicle 308, fluids, such as water, may be delivered for use with this type of system.

The illustration of different components in inspection environment 300 in FIGS. 4-9 are presented as some examples in which these components may be implemented. The illustration of these components is not meant to imply physical or architectural limitations to the manner in which an illustrative embodiment may be implemented. Other components may be used in addition to, and/or in place of, the ones illustrated. Further, the blocks illustrated in these figures may be combined or divided into different blocks depending on the particular implementation.

Figure 9:
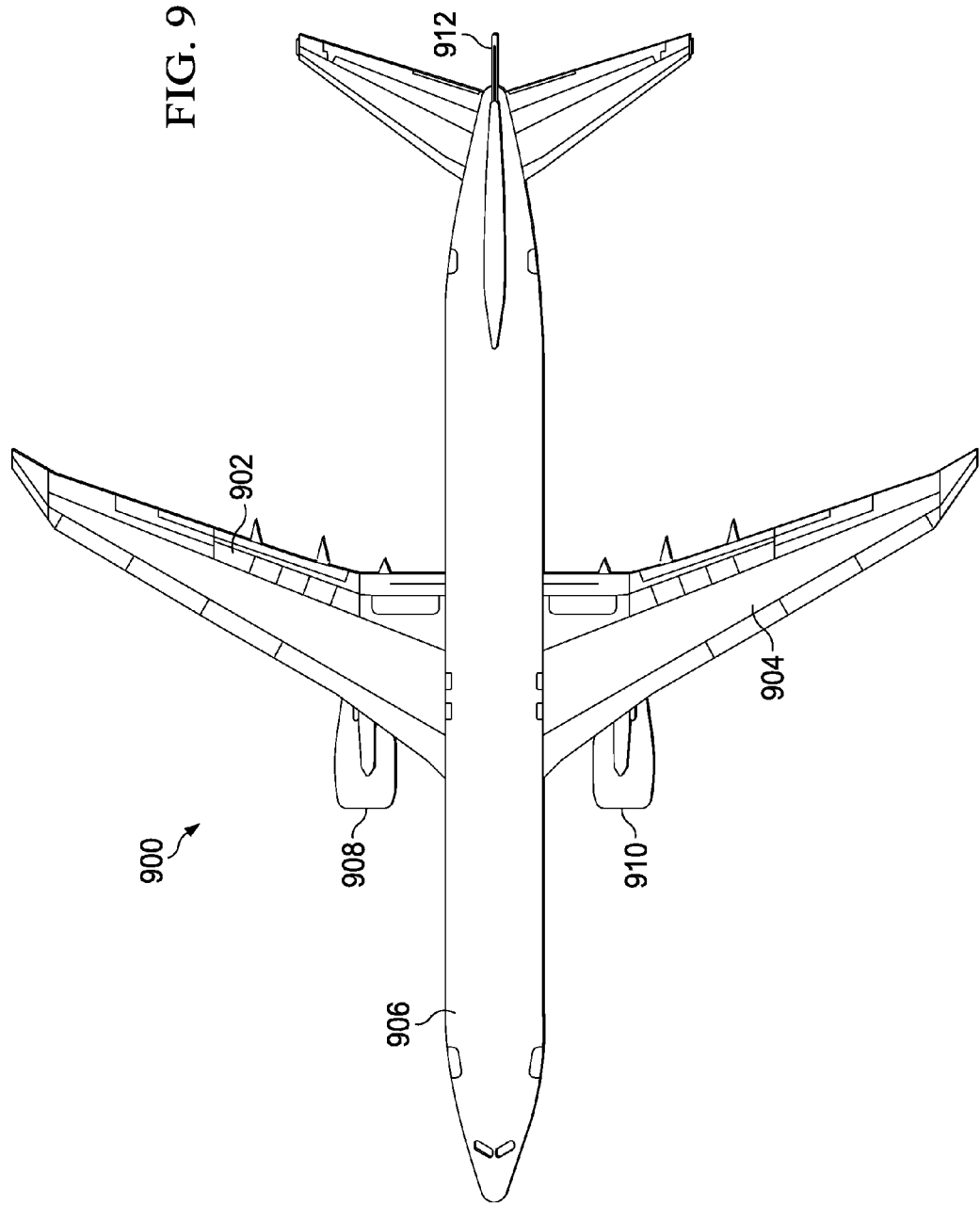
FIG. 9 is an illustration of an object on which inspections may be performed in accordance with an illustrative embodiment.

With reference now to FIG. 9, an illustration of an object on which inspections may be performed is depicted in accordance with an illustrative embodiment. In this illustrative example, aircraft 900 is an example of one implementation for object 306 in FIG. 3.

Aircraft 900 has wings 902 and 904. These wings are attached to fuselage 906. Aircraft 900 also includes engine 908, engine 910, and tail 912. Inspection may be performed on aircraft 900 using an inspection system in accordance with an illustrative embodiment.

Figure 10:
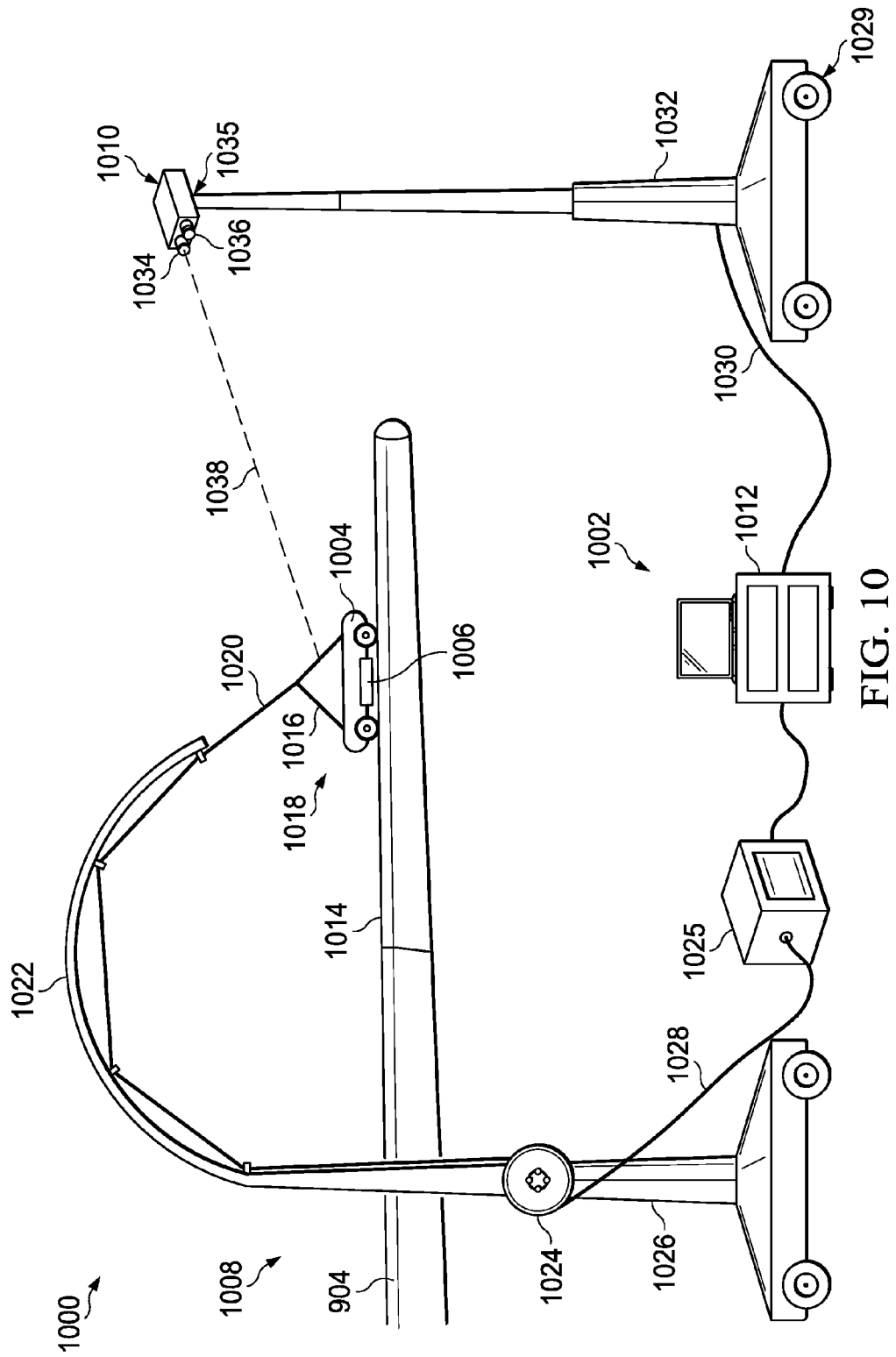
FIG. 10 is an illustration of an inspection environment in accordance with an illustrative embodiment.

With reference now to FIG. 10, an illustration of an inspection environment is depicted in accordance with an illustrative embodiment. Inspection environment 1000 is an example of one implementation of inspection environment 300 in FIG. 3. Inspection environment 1000 may be used to perform inspections on different parts of aircraft 900 in FIG. 9.

As illustrated, inspection system 1002 includes inspection vehicle 1004, sensor system 1006, support system 1008, positioning system 1010, and controller 1012. In this illustrative example, inspection vehicle 1004 moves on surface 1014 of wing 904.

Structure 1016 is associated with inspection vehicle 1004. Optical targets 1018 are attached to structure 1016. Optical targets 1018 may include, for example, light-emitting diodes, retro-reflective markers, and other suitable types of markers. Structure 1016 and optical targets 1018 are examples of components that may be used in optical marker system 522 in FIG. 5.

Sensor system 1006 is associated with inspection vehicle 1004 in a manner that allows sensor system 1006 to perform tests on wing 904. In this illustrative example, sensor system 1006 is located on a bottom side of inspection vehicle 1004. Of course, sensor system 1006 may be located on some other side of inspection vehicle 1004 in other implementations.

In this illustrative example, line system 1020 in support system 1008 is connected to inspection vehicle 1004. Line system 1020 is connected to inspection vehicle 1004 through structure 1016. Line system 1020 also is connected to rod 1022 and reel 1024 in support system 1008. Rod 1022 is a flexible rod in these illustrative examples and is connected to frame 1026.

Fluid tank and pump 1025 is connected to a fluid line in line system 1020. Fluid tank and pump 1025 may pump fluid through a fluid line in line system 1020 to sensor system 1006. The fluid may be used with sensor system 1006 when the system takes the form of an ultrasonic testing system.

Reel 1024 is mounted on frame 1026 in these illustrative examples. Reel 1024 is a tensionable reel in these examples. Reel 1024 may operate to change the tension in line system 1020. In these illustrative examples, line system 1020 includes a tether and a fluid line. In other illustrative examples, other lines also may be included, such as a power line, a data line, and other suitable types of lines.

Reel 1024 may be controlled by controller 1012 to selectively manage the movement of inspection vehicle 1004. Lines in line system 1020 may be reeled in or let out depending on the desired movement for inspection vehicle 1004. When reel 1024 is a tensionable reel, controller 1012 may not control reel 1024.

In these illustrative examples, controller 1012 is connected to support system 1008 and positioning system 1010. Controller 1012 is connected to the systems by cable 1028 and cable 1030. Cable 1028 connects controller 1012 to support system 1008. Cable 1030 connects controller 1012 to positioning system 1010. Cable 1028 and cable 1030 are electrical cables capable of carrying information, such as data and commands.

Positioning system 1010 comprises frame 1032, laser range meter 1034, pan-tilt unit 1035, and camera 1036. As depicted, frame 1032 has wheels 1029 and may be moveable. Positioning system 1010 may direct camera 1036, laser range meter 1034, and one or more of laser beams 1038 to optical targets 1018 to obtain information used to determine the position and orientation of inspection vehicle 1004.

The information generated by positioning system 1010 is sent to controller 1012. Controller 1012 then generates commands for inspection vehicle 1004 to direct movement of inspection vehicle 1004 on surface 1014 of wing 904. Additionally, controller 1012 also generates commands to operate sensor system 1006 on inspection vehicle 1004.

In these illustrative examples, controller 1012 communicates with inspection vehicle 1004 and sensor system 1006 through line system 1020.

Figure 11:
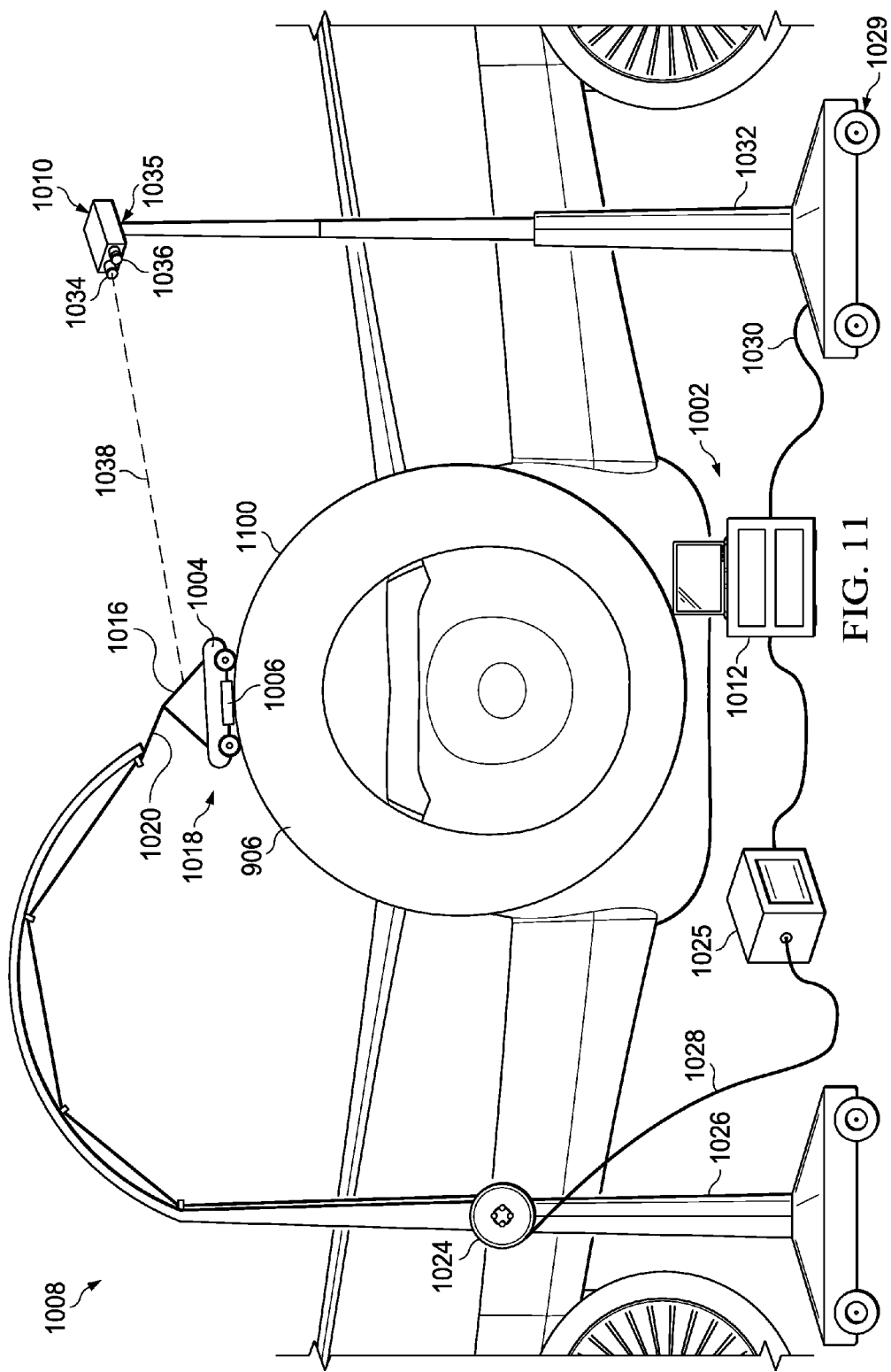
FIG. 11 is an illustration of an inspection environment in accordance with an illustrative embodiment.

With reference now to FIG. 11, an illustration of an inspection environment is depicted in accordance with an illustrative embodiment. In this illustrative example, inspection vehicle 1004 is shown on fuselage 906 of aircraft 900. As can be seen, support system 1008 may limit the fall of inspection vehicle 1004 if inspection vehicle 1004 loses traction and slips from surface 1100 of fuselage 906.

In this example, line system 1020 may be reeled in or extended to manage movement of inspection vehicle 1004. In this manner, the possibility of undesired consequences of slippage or some other undesired movement on surface 1100 of fuselage 906 by inspection vehicle 1004 may be reduced. In other illustrative examples, inspection vehicle 1004 may be prevented from falling off of fuselage 906.

Figure 12:
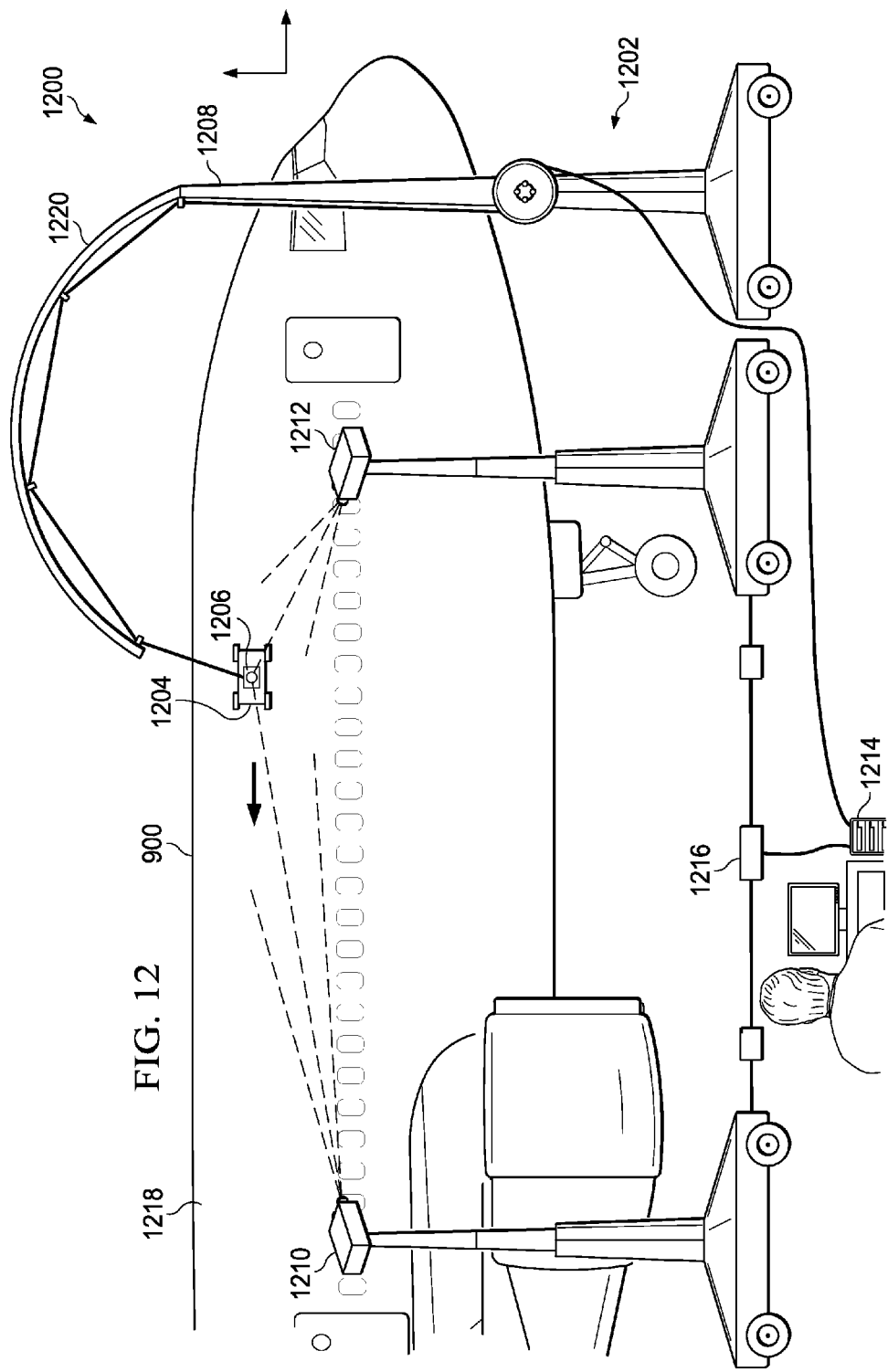
FIG. 12 is an illustration of an inspection environment in accordance with an illustrative embodiment.

With reference now to FIG. 12, an illustration of an inspection environment is depicted in accordance with an illustrative embodiment. In this illustrative example, inspection environment 1200 is another example of an implementation of inspection environment 300 in FIG. 3.

In this depicted example, inspection system 1202 includes inspection vehicle 1204 associated with sensor 1206. Inspection system 1202 also includes support system 1208, positioning system 1210, positioning system 1212 and controller 1214.

In this illustrative example, more than one positioning system is present in inspection system 1202. Positioning system 1210 and positioning system 1212 are connected to controller 1214 through switch 1216. With the use of additional positioning systems, more accurate measurements of the position and orientation of inspection vehicle 1204 on surface 1218 of aircraft 900 may be identified. Further, better coverage for different locations may be possible without moving a positioning system. In this illustrative example, support system 1208 has an elongate member in the form of boom 1220.

The illustration of the different inspection environments in FIGS. 10-12 are not meant to imply physical or architectural limitations to the manner in which an illustrative embodiment may be implemented. The different components shown in these figures may be combined with components used in FIGS. 3-8, used with components in FIGS. 3-8, or a combination of the two. Additionally, the different components illustrated in FIGS. 10-12 may be illustrative examples of how components shown in block form in FIGS. 3-8 may be implemented as physical structures.

Figure 13:
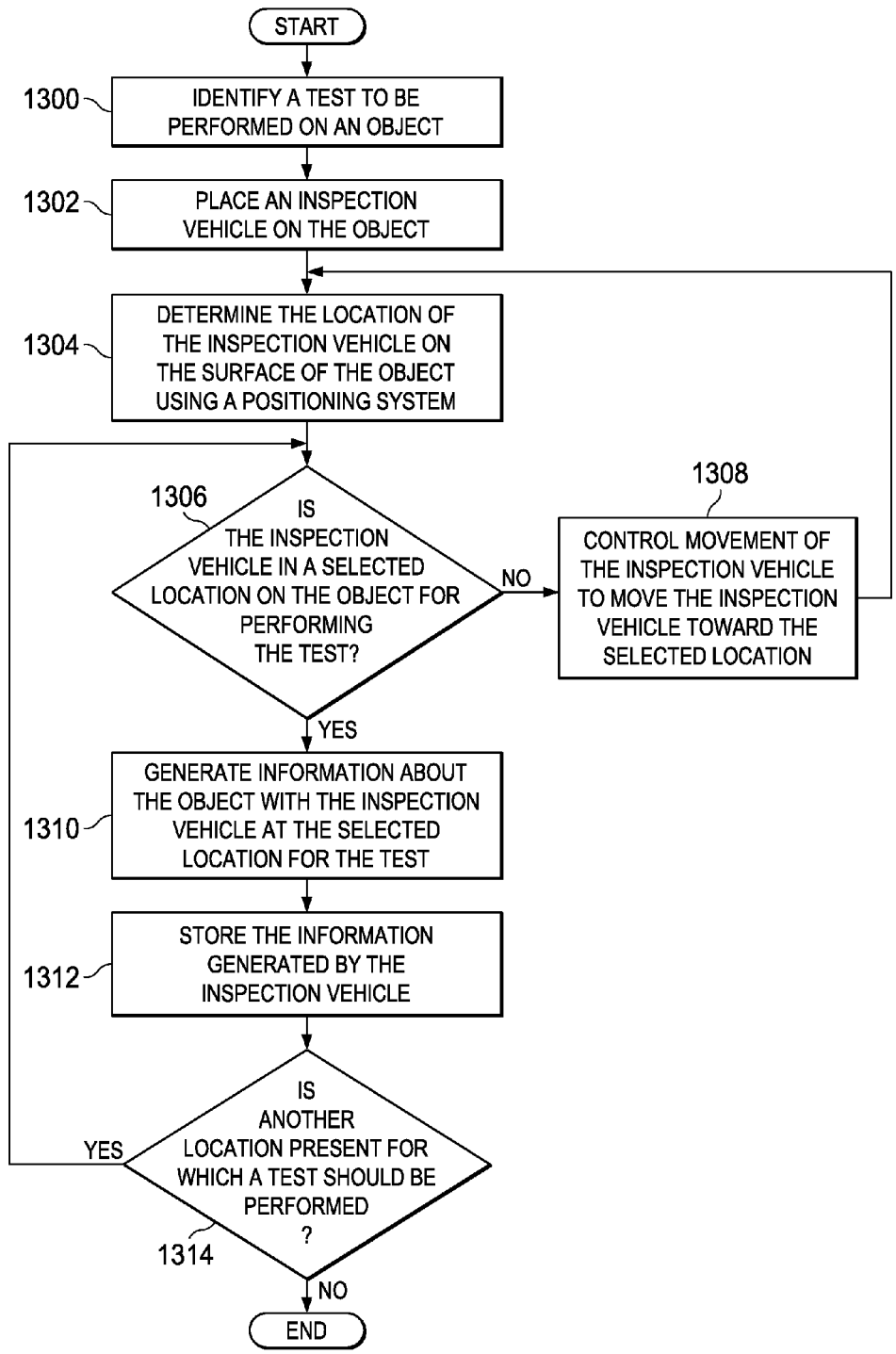
FIG. 13 is an illustration of a flowchart of a process for inspecting an object in accordance with an illustrative embodiment.

With reference now to FIG. 13, an illustration of a flowchart of a process for inspecting an object is depicted in accordance with an illustrative embodiment. The process illustrated in FIG. 13 may be implemented in inspection system 302 to perform inspections of object 306 in FIG. 3.

The process begins by identifying a test to be performed on an object (operation 1300). This test may be identified using a database, such as test database 412 in FIG. 4. The process may be implemented in hardware, software, or a combination of the two. For example, the process may be implemented in controller 316 in vehicle control module 404 and test module 406.

Thereafter, an inspection vehicle is placed on the object (operation 1302). The location of the inspection vehicle on the surface of the object is determined using location information generated by a positioning system (operation 1304).

A determination is made as to whether the inspection vehicle is in a selected location on the object for performing the test (operation 1306). If the vehicle is not in the selected location, the process controls the movement of the inspection vehicle to move the inspection vehicle toward the selected location (operation 1308), with the process then returning to operation 1304. Operation 1306 and operation 1308 may be part of a feedback control process for controlling the movement of the inspection vehicle.

Otherwise, information is generated about the object with the inspection vehicle at the location for the test (operation 1310). In operation 1310, information is generated about the object with the inspection vehicle by sending commands to a sensor system associated with the inspection vehicle. The process then stores the information generated by the inspection vehicle (operation 1312).

A determination is made as to whether another location is present for which a test should be performed (operation 1314). If another location is present, the process proceeds to operation 1306 as described above. Otherwise, the process terminates.

Figure 14:
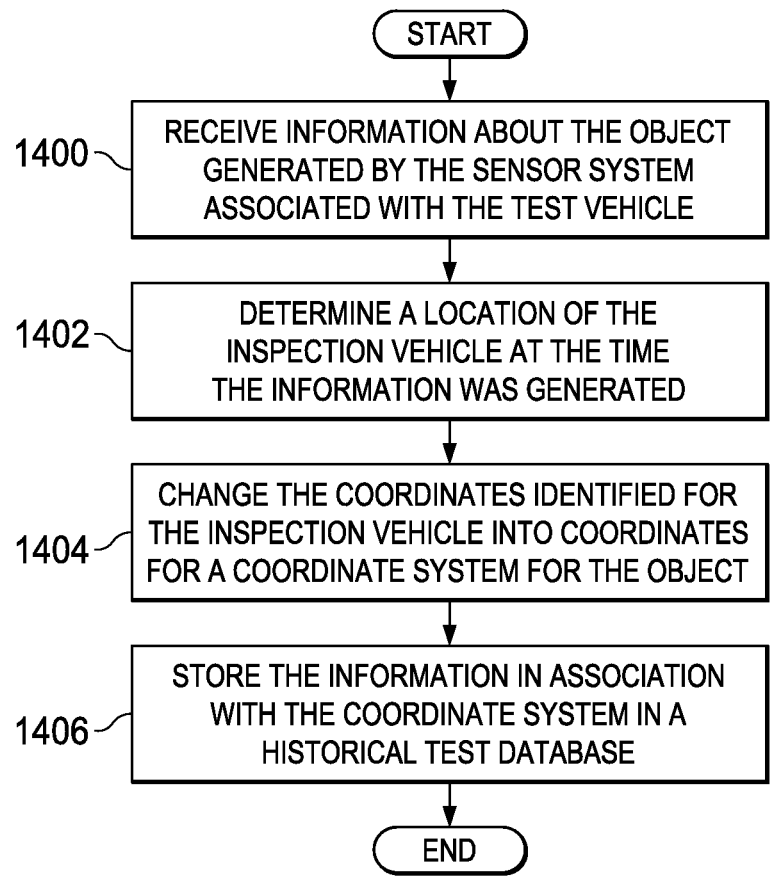
FIG. 14 is an illustration of a flowchart of a process for processing information received from a non-destructive evaluation system on an inspection vehicle in accordance with an illustrative embodiment.

With reference now to FIG. 14, an illustration of a flowchart of a process for processing information received from a sensor system on an inspection vehicle is depicted in accordance with an illustrative embodiment. The process illustrated in FIG. 14 may be implemented in inspection environment 300 in FIG. 3. In particular, this process may be implemented in test module 406 in controller 316 in FIG. 4. This process may be implemented using hardware, software, or a combination of the two. This process is an example of an implementation for operation 1312 in FIG. 13.

The process begins by receiving information about the object generated by the sensor system associated with the test vehicle (operation 1400). The process then determines a location of the inspection vehicle at the time the information was generated (operation 1402). The information received from the sensor system includes timestamps in these illustrative examples. In addition, location information generated by a positioning system also may include timestamps. These timestamps may be correlated to determine the location of the inspection vehicle at the time the information was generated.

The process then changes the coordinates identified for the inspection vehicle into coordinates for a coordinate system for the object (operation 1404). This coordinate system is one based on the object being inspected rather than some other object. This coordinate system may be one defined in a computer-aided design (CAD) model for the object.

The process then stores the information in association with the coordinate system in a historical test database (operation 1406). This historical test database may be, for example, historical test database 416. The information is stored with the coordinates and the date and time at which the test was performed. In this manner, other information recorded for the same coordinates on other dates may be analyzed with this information. The process then terminates. This operation may be performed each time information is to be stored in operation 1312 in FIG. 13.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the block may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Thus, the different illustrative embodiments provide a method and apparatus for non-destructive evaluation testing. A non-destructive evaluation system comprises an inspection vehicle, a sensor system, a positioning system, a controller, and a support system. The inspection vehicle is configured to move on a surface of an object. The sensor system is associated with the inspection vehicle and is configured to generate information about the object when the inspection vehicle is on the surface of the object.

The positioning system is configured to determine a location of the inspection vehicle on the object. The controller is configured to control movement of the inspection vehicle using the positioning system and control operation of the sensor system. The support system is connected to the inspection vehicle and is configured to support the inspection vehicle in response to an undesired release of the inspection vehicle from the surface of the object.

Thus, the different illustrative embodiments provide a capability to obtain information to determine whether inconsistencies are present in an aircraft. In particular, the different illustrative examples may be used to identify inconsistencies including undesired inconsistencies. With the different illustrative examples, lower cost inspection vehicles may be implemented. The controllers for these inspection vehicles may be used to control other vehicles rather than having a controller for each inspection vehicle.

Further, the different illustrative examples provide a management system to aide in managing the movement of the inspection vehicle for objects that may not have substantially planar surfaces or with surfaces that may be angled at undesired angles. For example, with the support system in the different illustrative examples, slippage or falling of an inspection vehicle may be addressed. Additionally, if an inspection vehicle falls or slips, damage to that inspection vehicle or the object that is being inspected may be reduced or avoided using support system 1008 in FIG. 10.

Also, with the inspection system 302 in FIG. 3, less operator time is needed to perform inspections of aircraft. As a result, less operator fatigue may occur. Further, with inspection system 302, a reduction in incorrect readings or tests in incorrect locations may occur.

Turning now to FIG. 15, an illustration of a data processing system is depicted in accordance with an illustrative embodiment. In this illustrative example, data processing system 1500 includes communications framework 1502, which provides communications between processor unit 1504, memory 1506, persistent storage 1508, communications unit 1510, input/output (I/O) unit 1512, and display 1514. Data processing system 1500 may be used to implement controller 316 in FIG. 3. In these illustrative examples, data processing system 1500 may be used to implement one or more of number of computers 402 in computer system 400 of FIG. 4.

Processor unit 1504 serves to execute instructions for software that may be loaded into memory 1506. Processor unit 1504 may be a number of processors, a multi-processor core, or some other type of processor, depending on the particular implementation. A number, as used herein with reference to an item, means one or more items. Further, processor unit 1504 may be implemented using a number of heterogeneous processor systems in which a main processor is present with secondary processors on a single chip. As another illustrative example, processor unit 1504 may be a symmetric multi-processor system containing multiple processors of the same type.

Memory 1506 and persistent storage 1508 are examples of storage devices 1516. A storage device is any piece of hardware that is capable of storing information, such as, for example, without limitation, data, program code in functional form, and/or other suitable information either on a temporary basis and/or a permanent basis. Storage devices 1516 also may be referred to as computer readable storage devices in these examples. Memory 1506, in these examples, may be, for example, a random access memory or any other suitable volatile or non-volatile storage device. Persistent storage 1508 may take various forms, depending on the particular implementation.

For example, persistent storage 1508 may contain one or more components or devices. For example, persistent storage 1508 may be a hard drive, a flash memory, a rewritable optical disk, a rewritable magnetic tape, or some combination of the above. The media used by persistent storage 1508 also may be removable. For example, a removable hard drive may be used for persistent storage 1508.

Communications unit 1510, in these examples, provides for communications with other data processing systems or devices. In these examples, communications unit 1510 is a network interface card. Communications unit 1510 may provide communications through the use of either or both physical and wireless communications links.

Input/output unit 1512 allows for input and output of data with other devices that may be connected to data processing system 1500. For example, input/output unit 1512 may provide a connection for user input through a keyboard, a mouse, and/or some other suitable input device. Further, input/output unit 1512 may send output to a printer. Display 1514 provides a mechanism to display information to a user.

Instructions for the operating system, applications, and/or programs may be located in storage devices 1516, which are in communication with processor unit 1504 through communications framework 1502. In these illustrative examples, the instructions are in a functional form on persistent storage 1508. These instructions may be loaded into memory 1506 for execution by processor unit 1504. The processes of the different embodiments may be performed by processor unit 1504 using computer implemented instructions, which may be located in a memory, such as memory 1506.

These instructions are referred to as program code, computer usable program code, or computer readable program code that may be read and executed by a processor in processor unit 1504. The program code in the different embodiments may be embodied on different physical or computer readable storage media, such as memory 1506 or persistent storage 1508.

Program code 1518 is located in a functional form on computer readable media 1520 that is selectively removable and may be loaded onto or transferred to data processing system 1500 for execution by processor unit 1504. Program code 1518 and computer readable media 1520 form computer program product 1522 in these examples. In one example, computer readable media 1520 may be computer readable storage media 1524 or computer readable signal media 1526. Computer readable storage media 1524 may include, for example, an optical or magnetic disk that is inserted or placed into a drive or other device that is part of persistent storage 1508 for transfer onto a storage device, such as a hard drive, that is part of persistent storage 1508.

Computer readable storage media 1524 also may take the form of a persistent storage, such as a hard drive, a thumb drive, or a flash memory, that is connected to data processing system 1500. In some instances, computer readable storage media 1524 may not be removable from data processing system 1500. In these examples, computer readable storage media 1524 is a physical or tangible storage device used to store program code 1518 rather than a medium that propagates or transmits program code 1518. Computer readable storage media 1524 is also referred to as a computer readable tangible storage device or a computer readable physical storage device. In other words, computer readable storage media 1524 is a media that can be touched by a person.

Alternatively, program code 1518 may be transferred to data processing system 1500 using computer readable signal media 1526. Computer readable signal media 1526 may be, for example, a propagated data signal containing program code 1518. For example, computer readable signal media 1526 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 1518 may be downloaded over a network to persistent storage 1508 from another device or data processing system through computer readable signal media 1526 for use within data processing system 1500. For instance, program code stored in a computer readable storage medium in a server data processing system may be downloaded over a network from the server to data processing system 1500. The data processing system providing program code 1518 may be a server computer, a client computer, or some other device capable of storing and transmitting program code 1518.

The different components illustrated for data processing system 1500 are not meant to provide architectural limitations to the manner in which different embodiments may be implemented. The different illustrative embodiments may be implemented in a data processing system including components in addition to or in place of those illustrated for data processing system 1500.

Other components shown in FIG. 15 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 1504 may take the form of a hardware unit that has circuits that are manufactured or configured for a particular use. This type of hardware may perform operations without needing program code to be loaded into a memory from a storage device to be configured to perform the operations.

For example, when processor unit 1504 takes the form of a hardware unit, processor unit 1504 may be a circuit system, an application specific integrated circuit (ASIC), a programmable logic device, or some other suitable type of hardware configured to perform a number of operations. With a programmable logic device, the device is configured to perform the number of operations.

The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 1518 may be omitted because the processes for the different embodiments are implemented in a hardware unit.

In still another illustrative example, processor unit 1504 may be implemented using a combination of processors found in computers and hardware units. Processor unit 1504 may have a number of hardware units and a number of processors that are configured to run program code 1518. With this depicted example, some of the processes may be implemented in the number of hardware units, while other processes may be implemented in the number of processors.

In another example, a bus system may be used to implement communications framework 1502 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of more devices that transmit data, receive data, or transmit and receive data. A communications unit may be, for example, a modem or a network adapter, two network adapters, or some combination thereof. Further, a memory may be, for example, memory 1506, or a cache, such as found in an interface and memory controller hub that may be present in communications framework 1502.

The description of the present disclosure has been presented for purposes of illustration and description, and is not intended to be exhaustive or limited to the disclosure in the form disclosed. Many modifications and variations will be apparent to those of ordinary skill in the art.

For example, although an illustrative embodiment has been described with respect to aircraft, the illustrative embodiment may be applied to other types of objects. For example, without limitation, other illustrative embodiments may be applied to a mobile platform, a stationary platform, a land-based structure, an aquatic-based structure, a space-based structure and/or some other suitable object. More specifically, the different illustrative embodiments may be applied to, for example, without limitation, a submarine, a bus, a personnel carrier, tank, a train, an automobile, a spacecraft, a space station, a satellite, a surface ship, a power plant, a dam, a manufacturing facility, a building, a roadway, and/or some other suitable object.

Further, different illustrative embodiments may provide different advantages as compared to other illustrative embodiments. The embodiment or embodiments selected are chosen and described in order to best explain the principles of the disclosure, the practical application, and to enable others of ordinary skill in the art to understand the disclosure for various embodiments with various modifications as are suited to the particular use contemplated.

What is claimed is:

1. An apparatus comprising:
an inspection vehicle including a movement system configured to move the inspection vehicle on a surface of an object, the inspection vehicle configured to attach to the surface of the object by at least one of a suction cup system, a pressure differential system, and a magnetic system;
a sensor system associated with the inspection vehicle and configured to generate information about the object when the inspection vehicle is on the surface of the object;
a positioning system configured to determine at least one of coordinate information and orientation information about a location of the inspection vehicle on the surface of the object, wherein the positioning system is independent and outside of the inspection vehicle;

a controller system configured to control movement of the inspection vehicle using the positioning system and control operation of the sensor system; and a support system connected to the inspection vehicle and configured to support the inspection vehicle in response to an undesired release of the inspection vehicle from the surface of the object.

2. The apparatus of claim 1 further comprising:
a marker system configured to provide information to the positioning system for use in determining the location of the inspection vehicle.

3. The apparatus of claim 2, wherein the marker system comprises:
a number of optical targets connected to the inspection vehicle.

4. The apparatus of claim 1, wherein the inspection vehicle, the sensor system, the positioning system, the controller system, and the support system are part of a non-destructive evaluation system.

5. The apparatus of claim 1, wherein the sensor system comprises at least one of an ultrasonic sensor system, an imaging system, an eddy current sensor system, a laser shearography system, a thermography system, a magnetic and optical imaging system, a magnetic and resistive sensor system, and an optical system.

6. The apparatus of claim 1, wherein the support system comprises:
an elongate member; and
a line system connected to the elongate member and to the inspection vehicle.

7. The apparatus of claim 6, wherein the support system further comprises:
a reel, wherein the reel is configured to hold a line in the line system and supply a level of tension to the line; and
a brake unit configured to reduce rotation of the reel when tension is present in the line.

8. The apparatus of claim 6, wherein the line system comprises at least one of a tether, a power line, a fluid transport line, and a data line.

9. The apparatus of claim 6, wherein the support system further comprises a line controller configured to control a set of lines connected to the line controller to perform at least one of supporting the inspection vehicle in response to the undesired release of the inspection vehicle from the surface of the object, slowing the movement of the inspection vehicle, halting the movement of the inspection vehicle, supporting the inspection vehicle as the inspection vehicle moves on the surface of the object, and lifting the inspection vehicle.

10. The apparatus of claim 9, wherein the line controller is configured to control the set of lines in response to a number of commands received from the controller system.

11. The apparatus of claim 1, wherein the positioning system comprises at least one of a camera system, a camera tracking system, a laser range meter, a global positioning system receiver, a motion capture positioning system, a laser tracking system, an inertial navigation positioning system, and a radio frequency identification receiver system.

12. The apparatus of claim 1, wherein the object is selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, a roadway, and a building.

13. A non-destructive evaluation inspection system for an aircraft comprising:

an inspection vehicle including a movement system configured to move the inspection vehicle on a surface of the aircraft, the inspection vehicle configured to attach to the surface of the aircraft by at least one of a suction cup system, a pressure differential system, and a magnetic system;

a sensor system connected to the inspection vehicle and configured to obtain information about the aircraft when the inspection vehicle is on the surface of the aircraft;

a support system comprising a reel, an elongate member, and a number of lines connected to the elongate member and the inspection vehicle, wherein the support system is configured to support the inspection vehicle in response to an undesired release of the inspection vehicle from the surface of the aircraft;

a positioning system configured to determine at least one of coordinate information and orientation information about a location of the inspection vehicle on the surface of the aircraft, wherein the positioning system is independent and outside of the inspection vehicle; and a controller system configured to control movement of the inspection vehicle using the positioning system and control operation of the sensor system.

14. A method for inspecting an object, the method comprising:
determining at least one of coordinate information and orientation information about a location of an inspection vehicle on a surface of the object using a positioning system, wherein the positioning system is independent and outside of the inspection vehicle;
generating information about the object using a sensor system connected to the inspection vehicle while the inspection vehicle is on the surface of the object;
controlling movement of the inspection vehicle using a controller system, wherein the inspection vehicle includes a movement system configured to move the inspection vehicle on the surface of the object, the inspection vehicle attaching to the surface of the object by at least one of a suction cup system, a pressure differential system, and a magnetic system; and
supporting the inspection vehicle in response to an undesired release of the inspection vehicle from the surface of the object using a support system connected to the inspection vehicle.

15. The method of claim 14 further comprising:
storing the information generated about the object in a historical test database.

16. The method of claim 15, wherein storing the information generated about the object in the historical test database comprises:
determining coordinates for the information using a coordinate system for a model of the object;
identifying a date of when the information was generated; and
storing the information generated about the object in the historical test database with the coordinates and the date.

17. The method of claim 14, wherein supporting the inspection vehicle in response to the undesired release of the inspection vehicle from the surface of the object comprises:
limiting at least one of a type and range of motion of the inspection vehicle to reduce a possibility of the undesired release of the inspection vehicle causing undesired effects to at least one of the inspection vehicle and the object.

18. The method of claim 14 further comprising:
   determining whether an inconsistency is present at a location on the object using the information generated by the sensor system at the location; and
   responsive to a determination that the inconsistency is present at the location on the object, tagging the location on the object using a tagging system.

19. The method of claim 14, wherein the sensor system comprises at least one of an ultrasonic testing system, an imaging system, an eddy current sensor system, a laser shearography system, a thermography system, a magnetic and optical imaging system, a magnetic and resistive sensor system, and an optical system.

20. The method of claim 14, wherein the step of determining the location of the inspection vehicle on the surface of the object using the positioning system comprises:
   generating location information using the positioning system and information received from a marker system; and
   determining the location of the inspection vehicle on the surface of the object with respect to a coordinate system for the object using the location information and a model for the object.

\* \* \* \* \*